(12) United States Patent
Ahn et al.

(10) Patent No.: US 11,446,254 B2
(45) Date of Patent: Sep. 20, 2022

(54) DRUG CARRIER HAVING SELF-ASSEMBLED 3-D NUCLEIC ACID NANOSTRUCTURE

(71) Applicant: KOREA INSTITUTE OF SCIENCE AND TECHNOLOGY, Seoul (KR)

(72) Inventors: Dae Ro Ahn, Seoul (KR); Se Hoon Kim, Seoul (KR); Kyoung Ran Kim, Seoul (KR); Hyo Young Kim, Seoul (KR); Yong Deok Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 155 days.

(21) Appl. No.: 16/538,109

(22) Filed: Aug. 12, 2019

(65) Prior Publication Data
US 2019/0365659 A1    Dec. 5, 2019

Related U.S. Application Data

(62) Division of application No. 14/803,343, filed on Jul. 20, 2015, now abandoned.

(30) Foreign Application Priority Data

Jul. 23, 2014  (KR) ........................ 10-2014-0093458

(51) Int. Cl.
| | | |
|---|---|---|
| A61K 9/51 | (2006.01) | |
| A61P 35/00 | (2006.01) | |
| A61K 49/00 | (2006.01) | |
| A61K 31/704 | (2006.01) | |
| A61K 9/00 | (2006.01) | |

(Continued)

(52) U.S. Cl.
CPC ............ *A61K 9/513* (2013.01); *A61K 9/0019* (2013.01); *A61K 31/704* (2013.01); *A61K 31/7088* (2013.01); *A61K 31/713* (2013.01); *A61K 38/02* (2013.01); *A61K 47/549* (2017.08); *A61K 49/0002* (2013.01); *A61K 49/0032* (2013.01);

(Continued)

(58) Field of Classification Search
CPC .. A61K 9/513; A61K 31/7088; A61K 31/713; A61P 35/00
See application file for complete search history.

(56) References Cited

U.S. PATENT DOCUMENTS

| | | |
|---|---|---|
| 7,858,770 B2 | 12/2010 | Lee et al. |
| 9,266,844 B2 | 2/2016 | Sarafianos et al. |
| 2009/0192100 A1 | 7/2009 | Vater et al. |

FOREIGN PATENT DOCUMENTS

| | | |
|---|---|---|
| KR | 101494773 B1 | 2/2015 |
| WO | 2007/122405 A1 | 11/2007 |
| WO | 2012/125987 A2 | 9/2012 |

OTHER PUBLICATIONS

DeVries et al, J. Controlled Release 172: 467-483, 2013; available online Jun. 3, 2013.*

(Continued)

*Primary Examiner* — Kevin K Hill
(74) *Attorney, Agent, or Firm* — Frank Gao, esq.

(57) ABSTRACT

The present invention relates to a molecule delivery technology and a carrier technology, which may selectively deliver a material to a desired specific cell and living tissue. The present invention may be utilized in the field of a drug carrier which effectively delivers an imaging probe and a therapeutic agent to an affected part.

9 Claims, 24 Drawing Sheets
(21 of 24 Drawing Sheet(s) Filed in Color)
Specification includes a Sequence Listing.

(51) Int. Cl.
    *A61K 47/54*    (2017.01)
    *A61K 31/7088*  (2006.01)
    *A61K 31/713*   (2006.01)
    *A61K 38/02*    (2006.01)

(52) U.S. Cl.
    CPC ...... *A61K 49/0043* (2013.01); *A61K 49/0054* (2013.01)

(56) References Cited

OTHER PUBLICATIONS

Zhang et al., ACS Nano 8(7): 6633-6643, 2014; available Jun. 25, 2014.*

Lin et al, NanoLetters 9(1):433-436, 2009.*

Jean-Luc Bridot, et al; "Hybrid Gadolinium Oxide Nanoparticles: Multimodal Contrast Agents for in Vivo Imaging", J. Am. chem. Soc. Published on Web Mar. 31, 2007; vol. 129, pp. 5076-5084.

Microsugar Chang, et al; "Aptamer-Conjugated DNA Icosahedral Nanoparticles as a Carrier of Doxorubicin for Cancer Therapy", ACS NANO; Published online Jul. 3, 2011; vol. 5, No. 8, pp. 6156-6163.

Jie Chao, et al; "Structural DNA Nanotechnology for Intelligent Drug Delivery", Small, Nov. 2014. 10(22): 4625-35; Epub. Jun. 23, 2014.

Jan Willem de Vries, et al; "Drug delivery systems based on nucleic add nanostructures", Journal of Controlled Release; vol. 172, pp. 467-483, Available online Jun. 3, 2013.

Kyoung-Ran Kim, et al; "Drug Delivery by a self-assembled DNA tetrahedron for overcoming drug resistance in breast cancer cells", Chem Commun. vol. 49, pp. 2010-2012; Available online Jan. 21, 2013.

Kyoung-Ran Kim, et al; "Utilizing the bioorthogonal base-pairing system of L-DNA to design ideal DNA nanocarriers for enhanced delivery of nucleic acid cargos", Chemical Science, vol. 5, pp. 1533-1537; Published Jan. 6, 2014.

Kyoung-Ran Kim, et al; "Sentinel lymph node imaging by a fluorescently labeled DNA tetrahedron", Biomaterials, vol. 34, p. 5226-5235, available online Apr. 12, 2013.

Hisataka Kobayashi; et al; "Improving Conventional Enhanced Permeability and Retention (EPR) Effects; What is the Appropriate Target?", Theranostics; vol. 4, Issue 1, pp. 81-89; available online Dec. 12, 2013.

Hyukjin Lee, et al; "Molecularly Self-Assembled Nucleic Acid Nanoparticles for Targeted in Vivo siRNA Delivery", Nature Nanotech; vol. 7, pp. 389-393; Available online Jun. 3, 2012.

Werner Likussar, et al; "Theory of Continuous Variations Plots and a New Method for Spectrophotometric Determination of Extraction and Formation Constants", Analytical Chemistry, vol. 43, No. 19, Aug. 1971; pp. 1265-1272.

Chenxiang Lin, et al; "Mirror image DNA Nanostructures far Chiral Supramolecular Assemblies", Nano Letters, vol. 9. No. 1, pp. 433-436, Published on Web Dec. 8, 2009.

Hyon Bin Na, et al; "Development of a T1 Contrast Agent for Magnetic Resonance Imaging Using MnO Nanoparticles". Angewandte Chem. Int. Ed. Vol. 46, Issue 28, Jul. 9, 2007; pp. 5397-5401.

Cuichen Wu, et al.; "Building a Multifunctional Aptamer-Based DNA Nanoassembly for Targeted Cancer Therapy", Journal of the American Chemical Society, vol. 135, pp. 18644-18650; Published Nov. 18, 2013.

Extended European Search Report dated Dec. 22, 2015; Appln. No. 15177301.7.

Korean Office Action dated Dec. 12, 2016; Appln. No. 10-2015-0101204.

* cited by examiner

[Fig. 1]
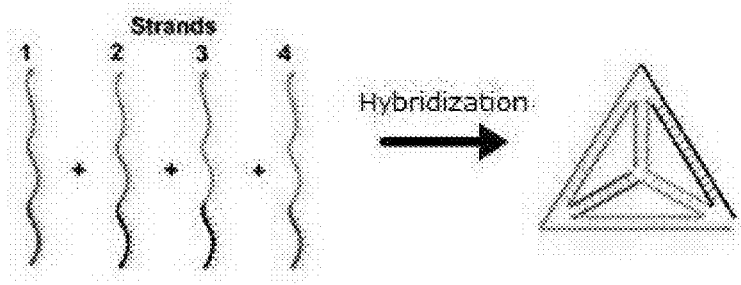
[Fig. 2a]
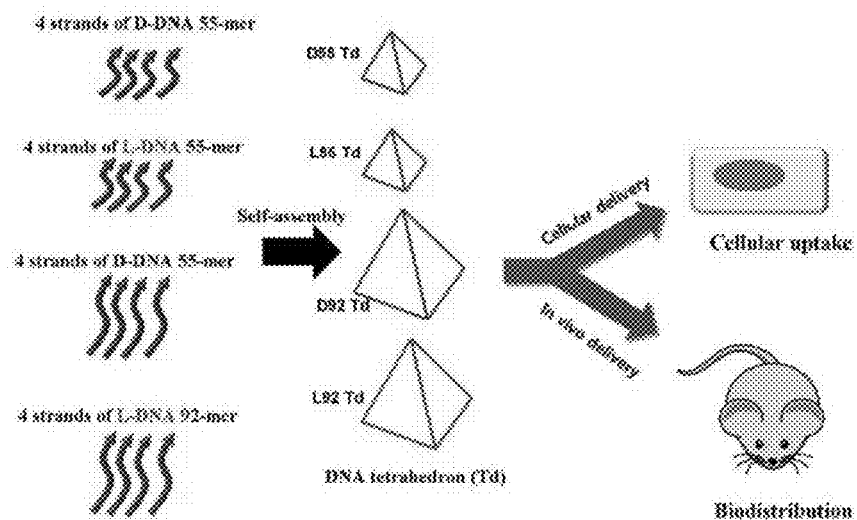
[Fig. 2b]
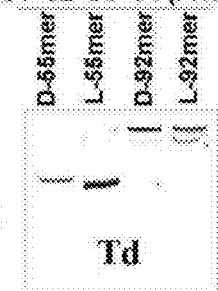

[Fig. 3a]
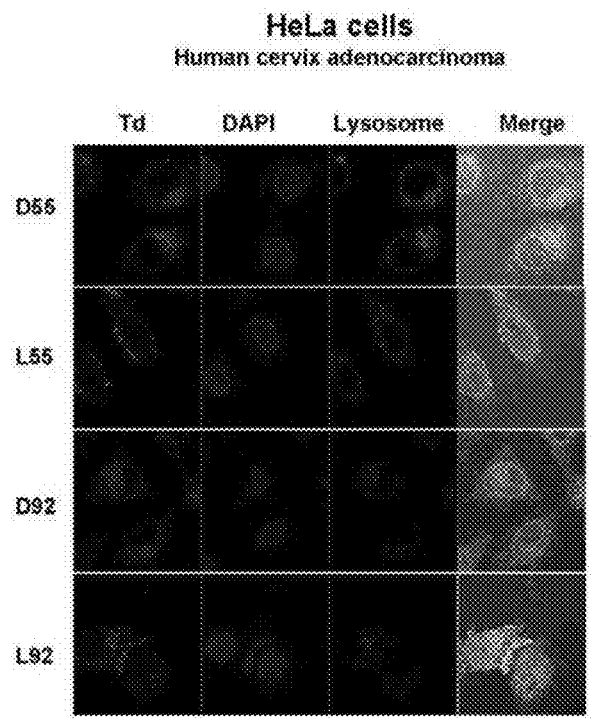
[Fig. 3b]
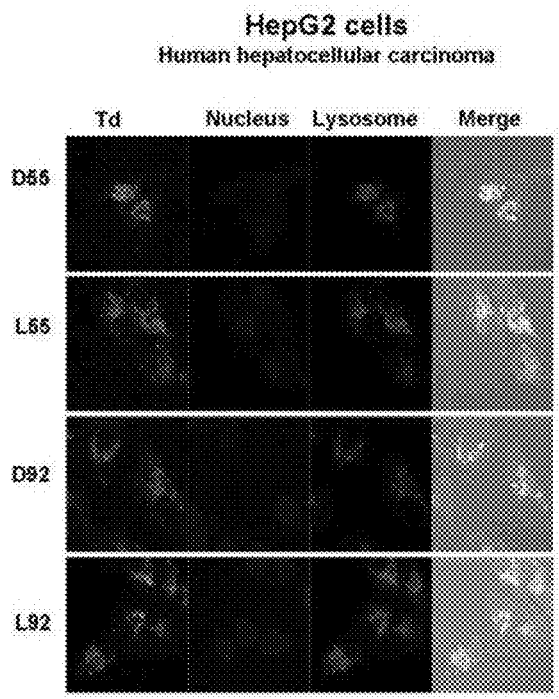

[Fig. 3c]
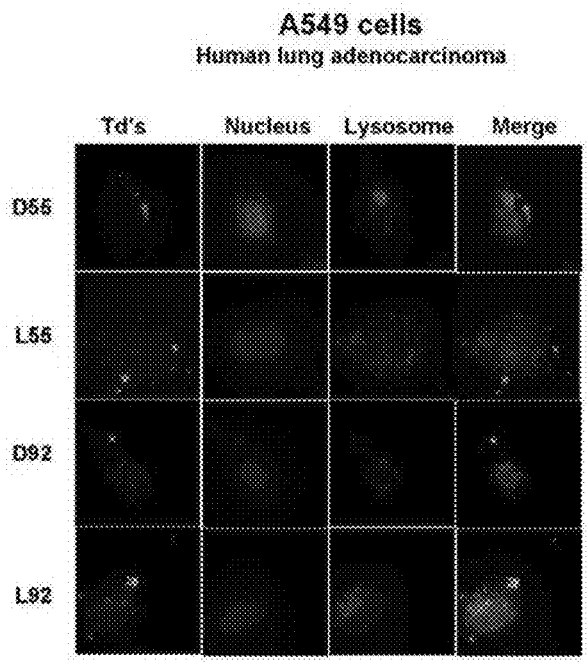
[Fig. 3d]
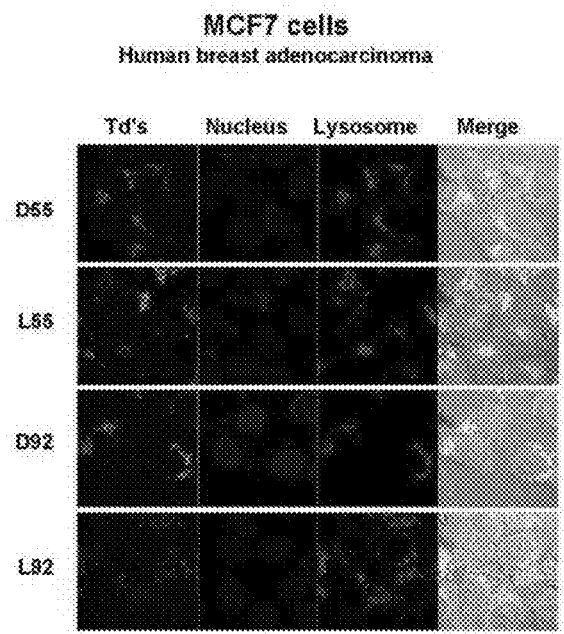

[Fig. 4]
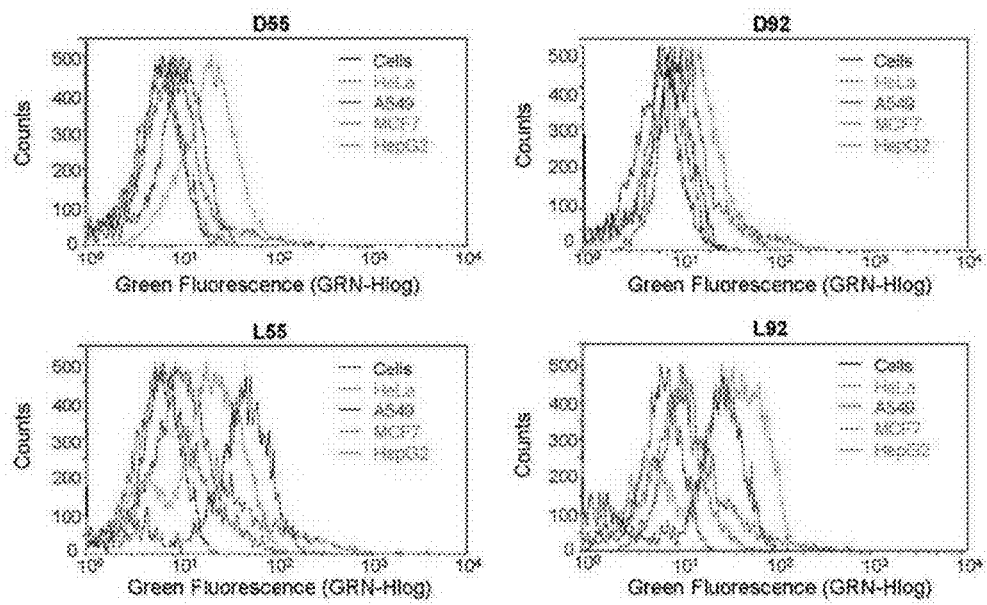
[Fig. 5a]
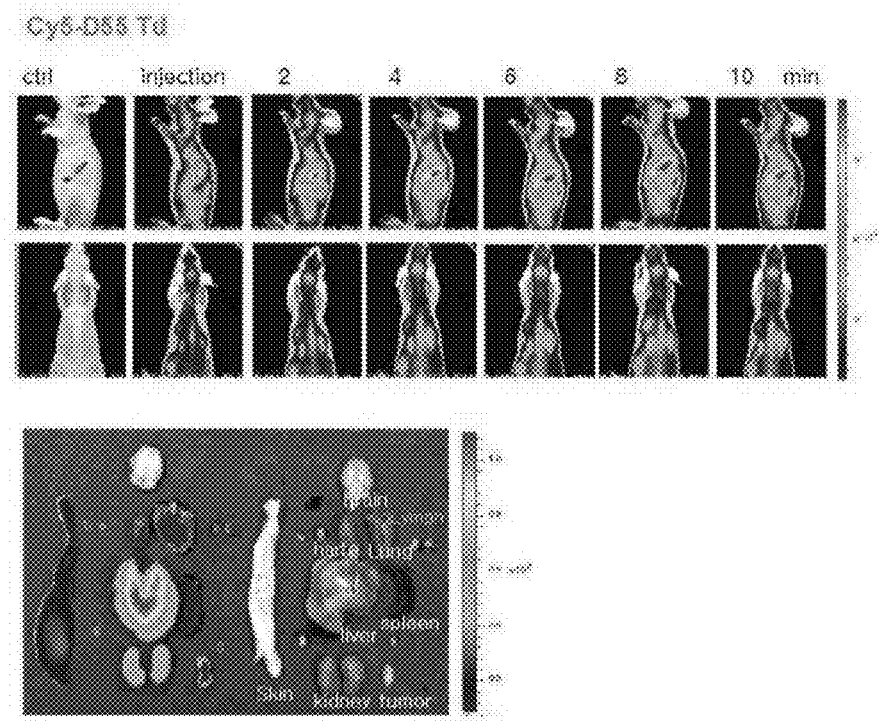

[Fig. 5b]
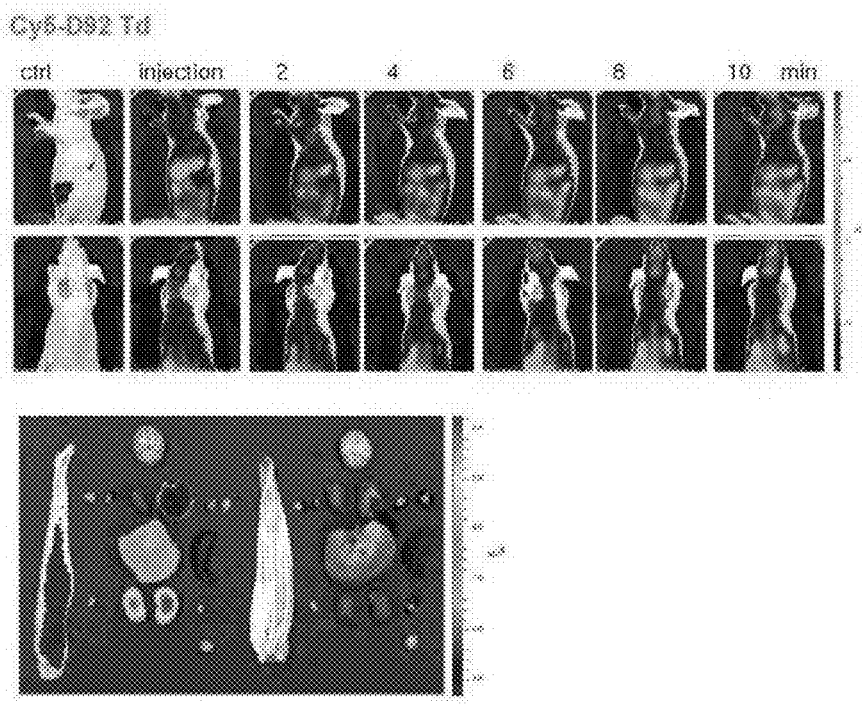
[Fig. 5c]
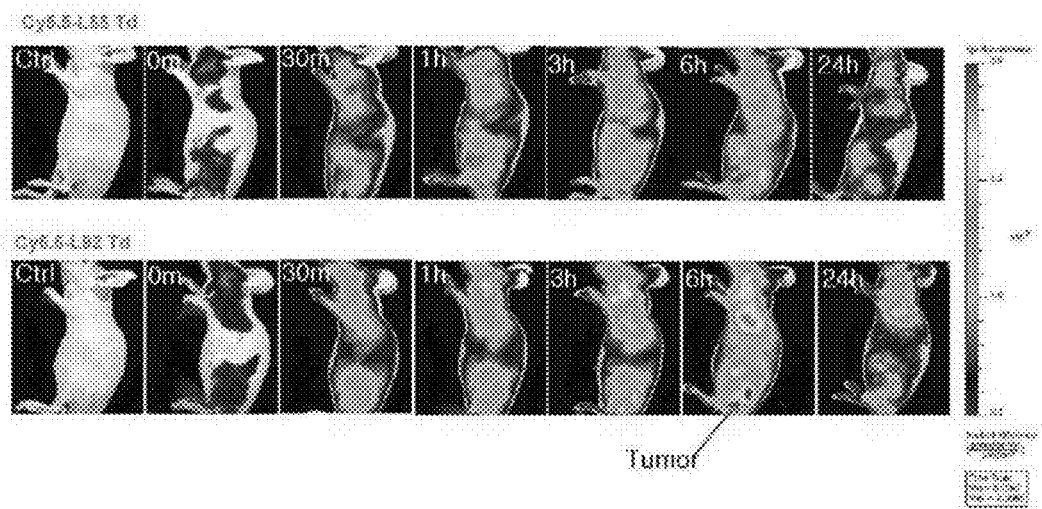

[Fig. 5d]
L55-cy5.5 (0.5 uM)
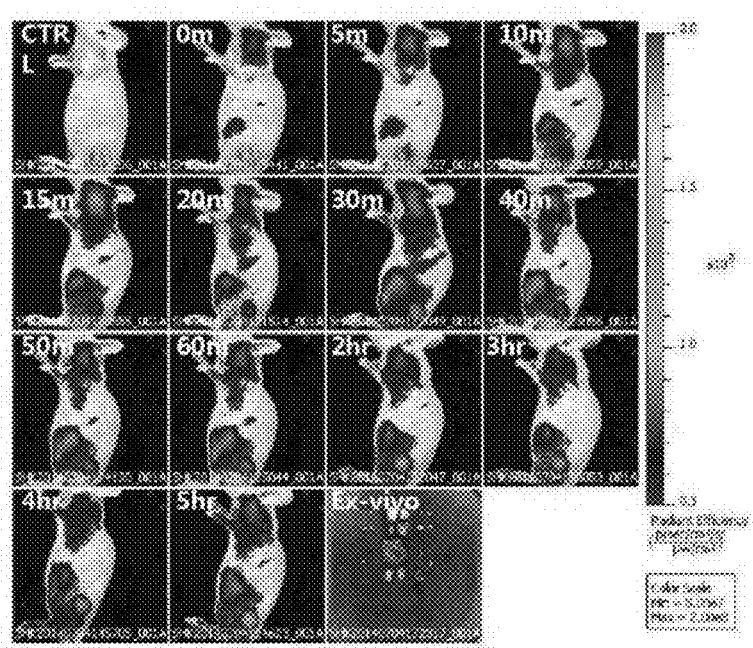
[Fig. 5e]
L92-cy5.5 (0.5 uM)
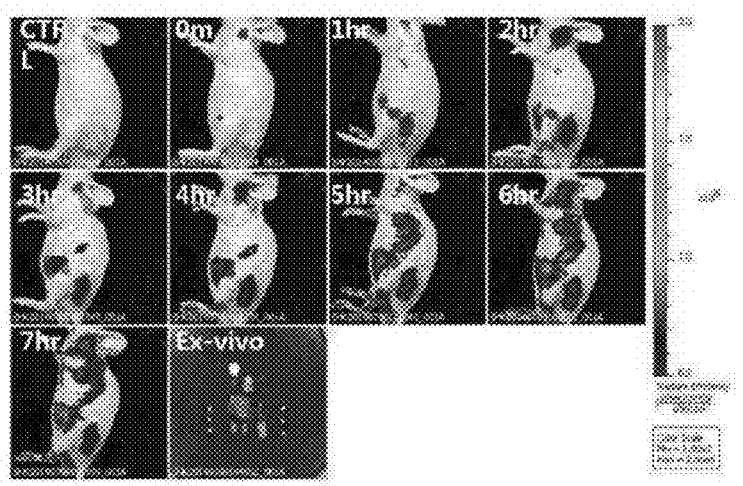

[Fig. 5f]
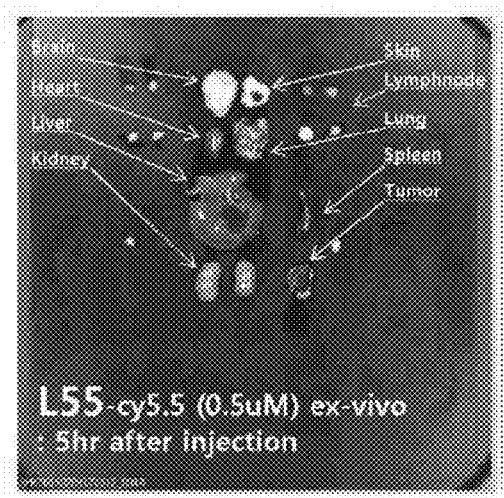
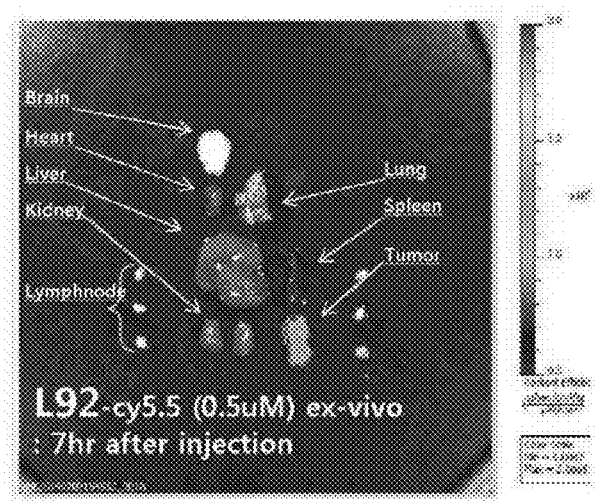
[Fig. 5g]
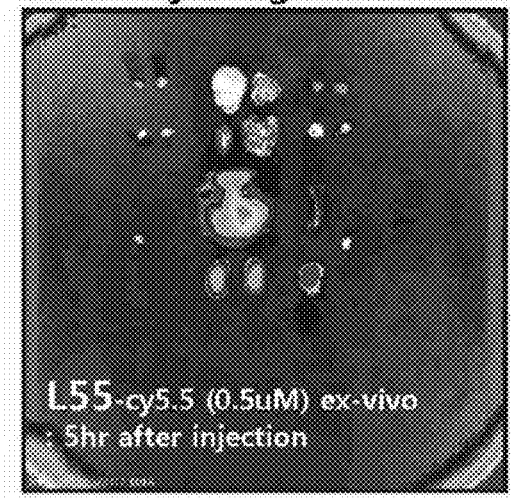

[Fig. 6a]
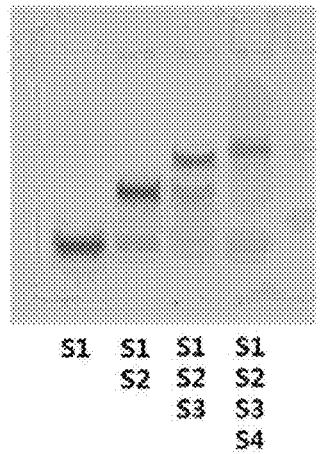
[Fig. 6b]
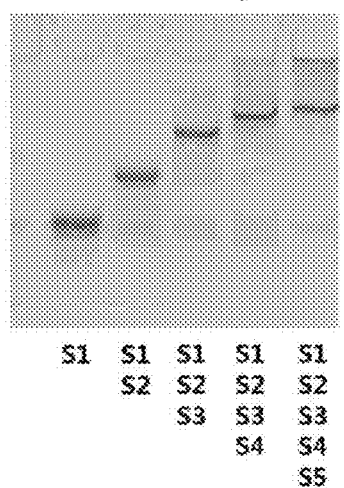

[Fig. 6c]
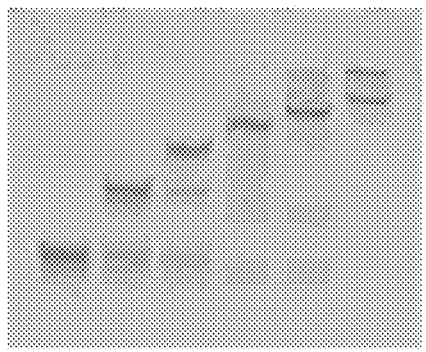
[Fig. 6d]
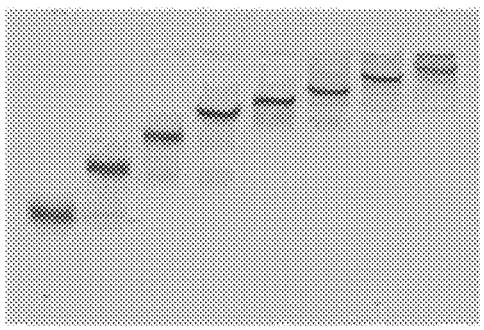

[Fig. 7a]
Free dye – *in vivo* imaging
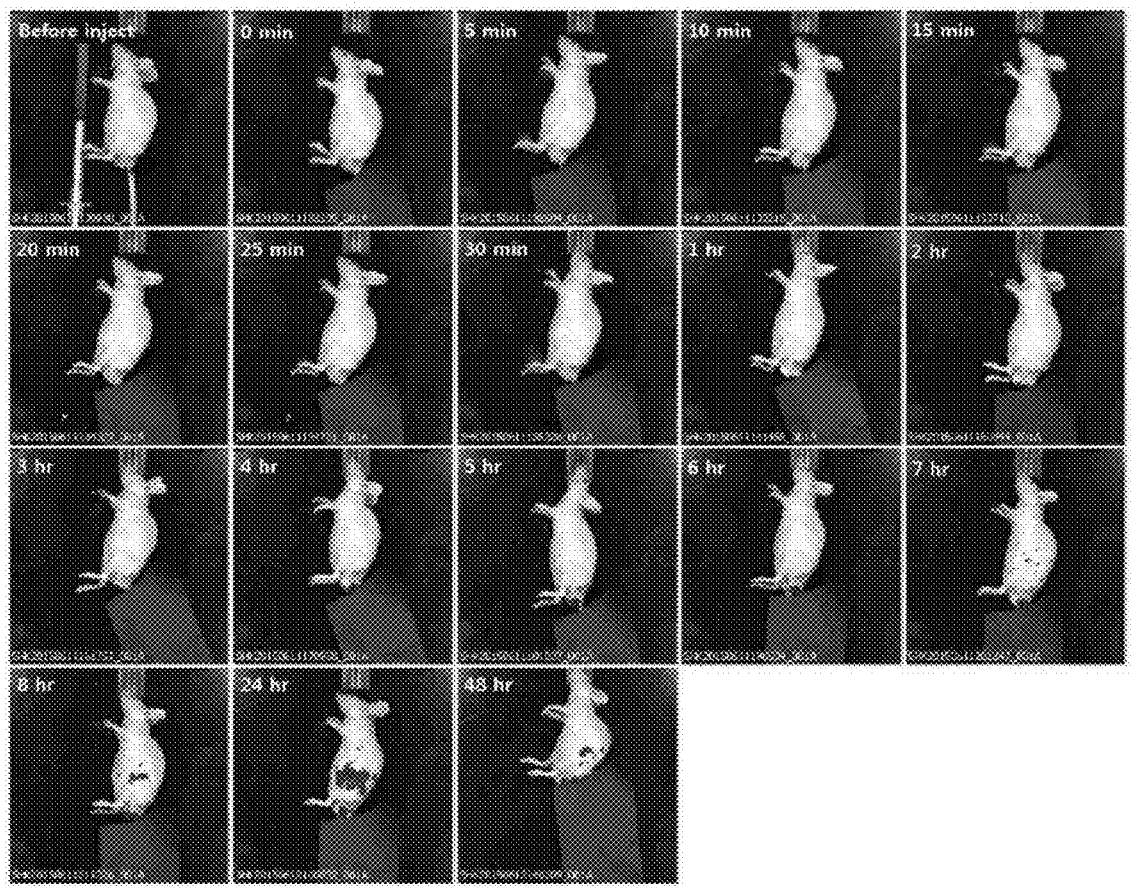

[Fig. 7b]
L-Tetrahedron (L-Td) - *in vivo* imaging
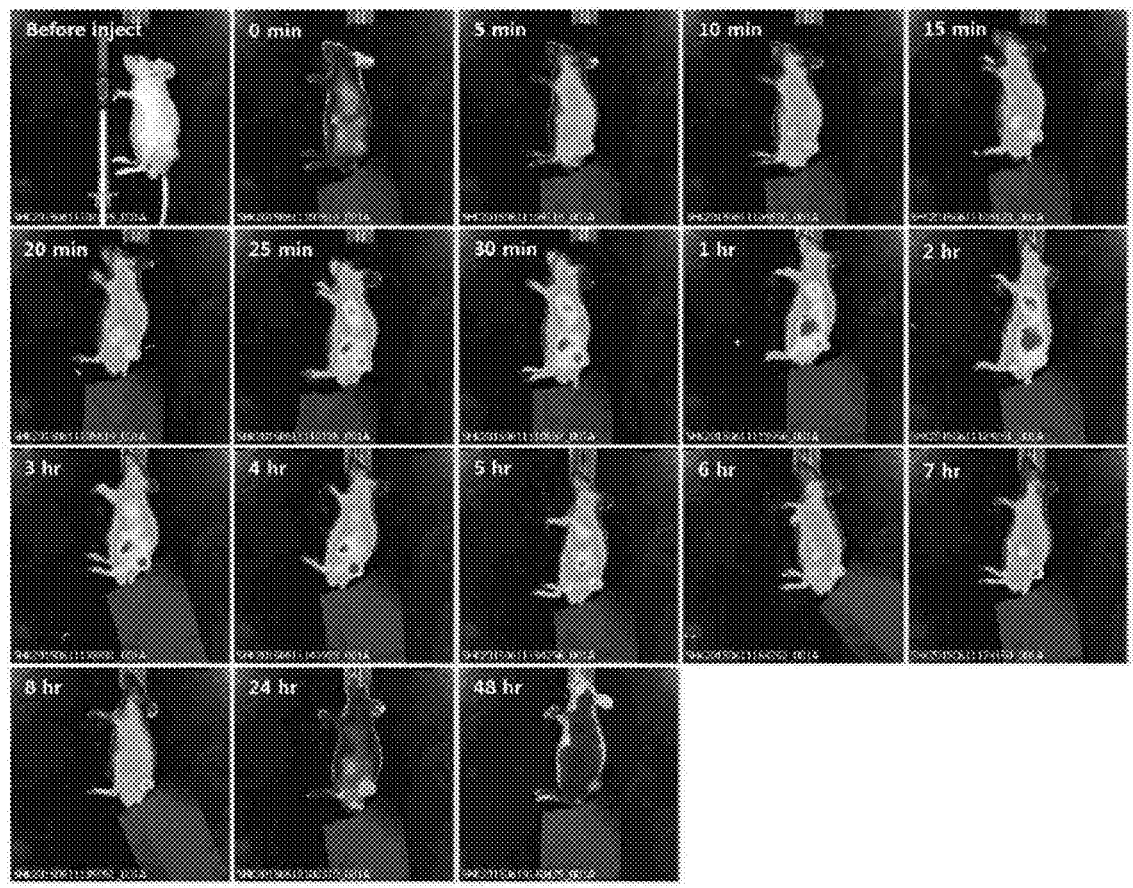

[Fig. 7c]
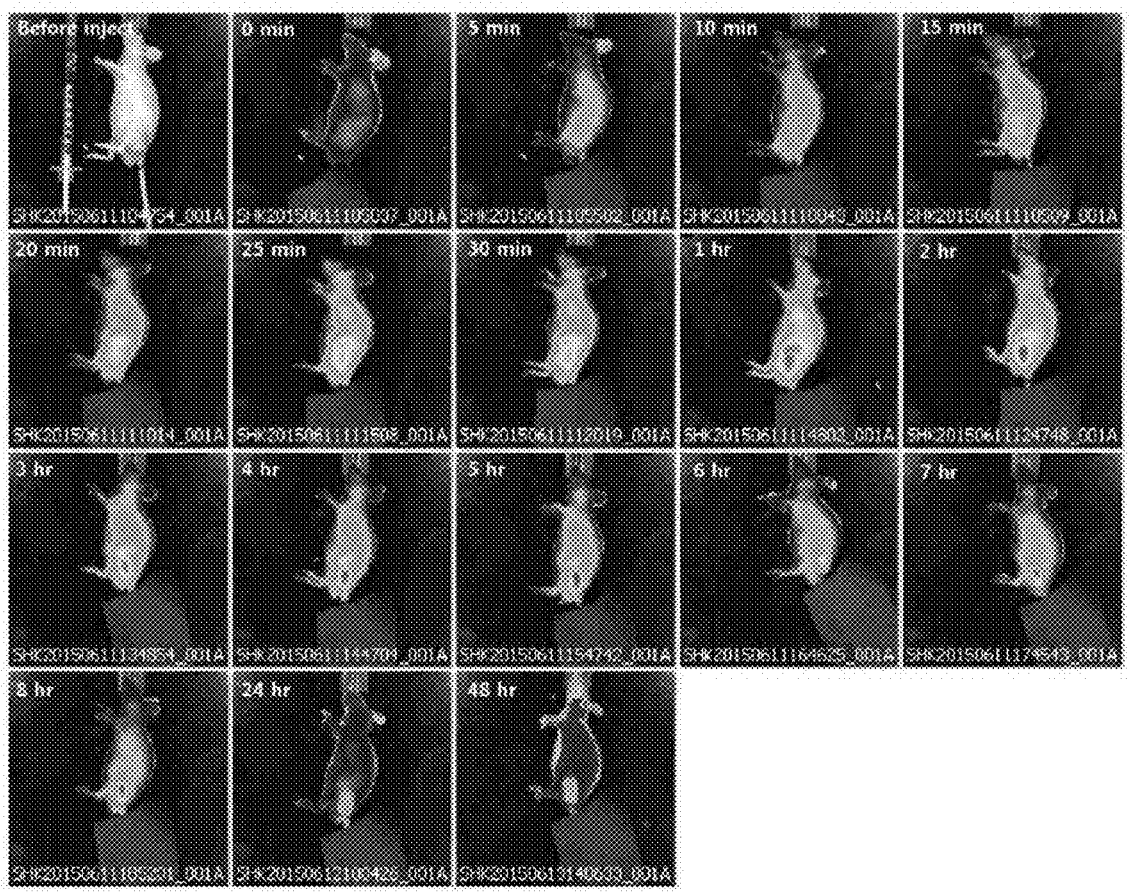

[Fig. 7d]
L-Cube (L-Cb) - *in vivo* imaging
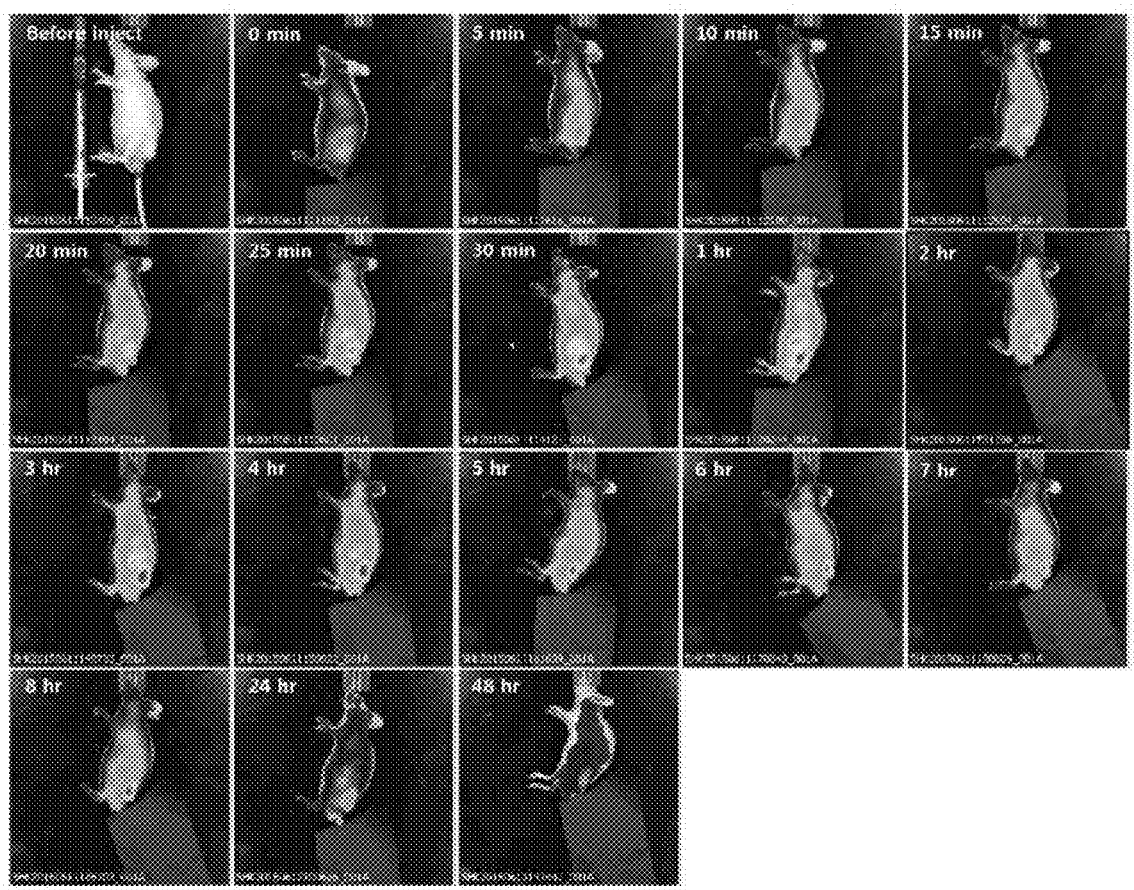

[Fig. 7e]
L-Octahedron (L-Od)-*in vivo* imaging
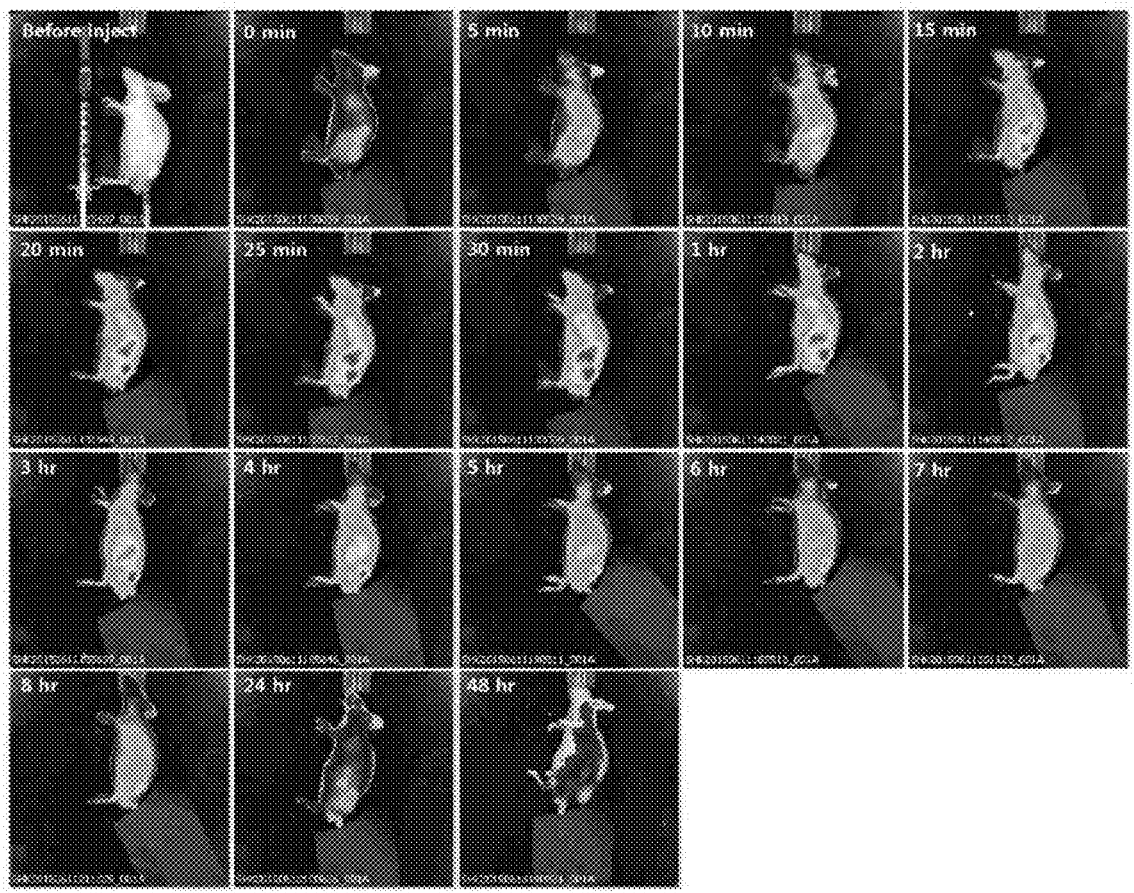

[Fig. 7f]
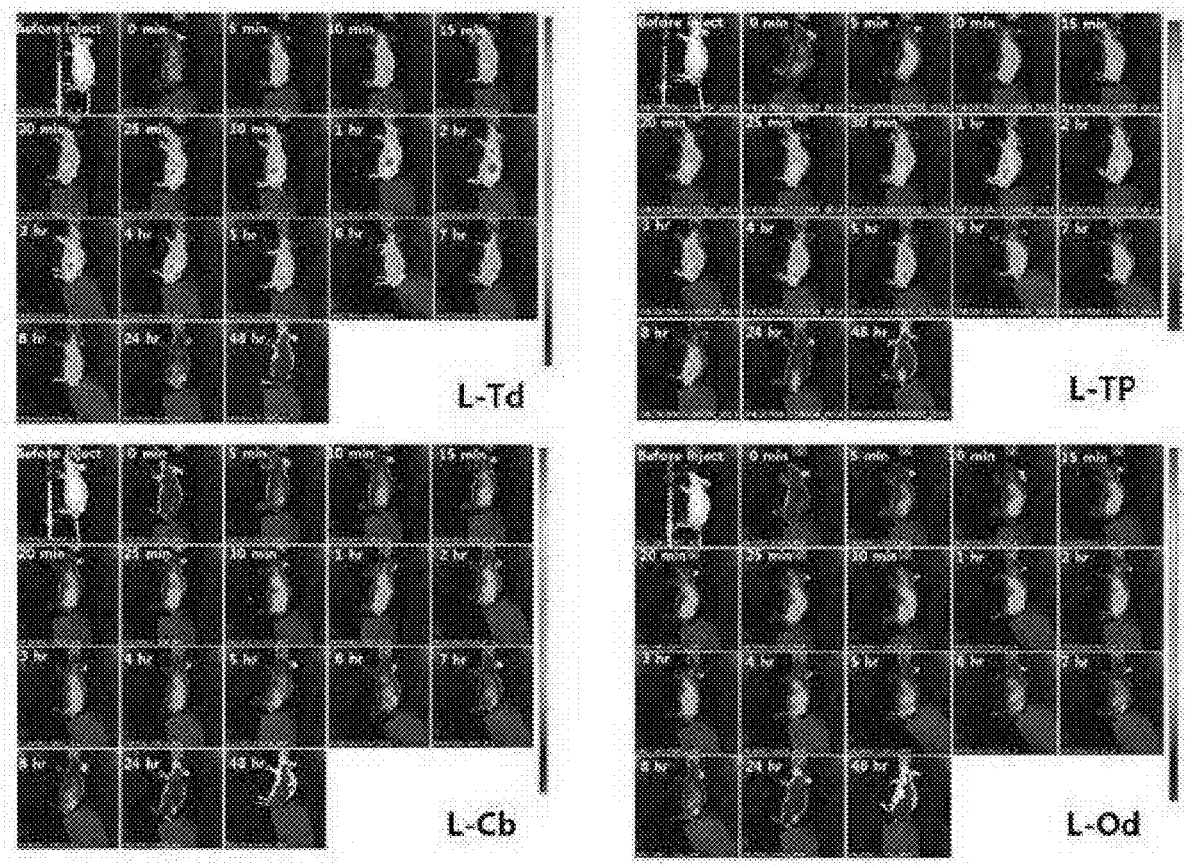

[Fig. 8a]
Free dye – *ex vivo* (4 h)
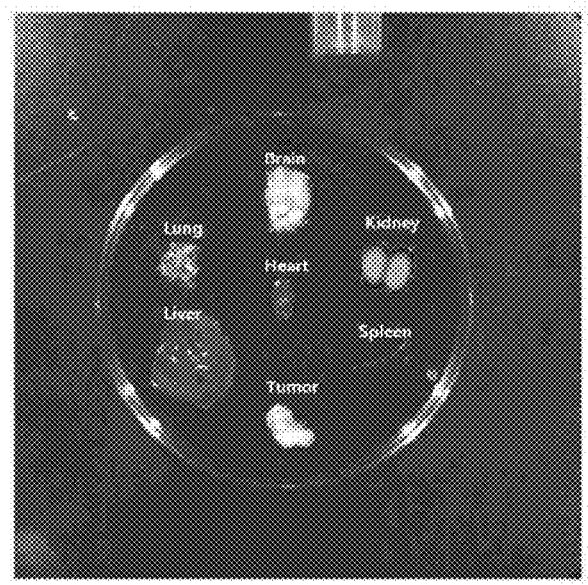
[Fig. 8b]
L-Tetrahedron (L-Td) – *ex vivo* (4 h)
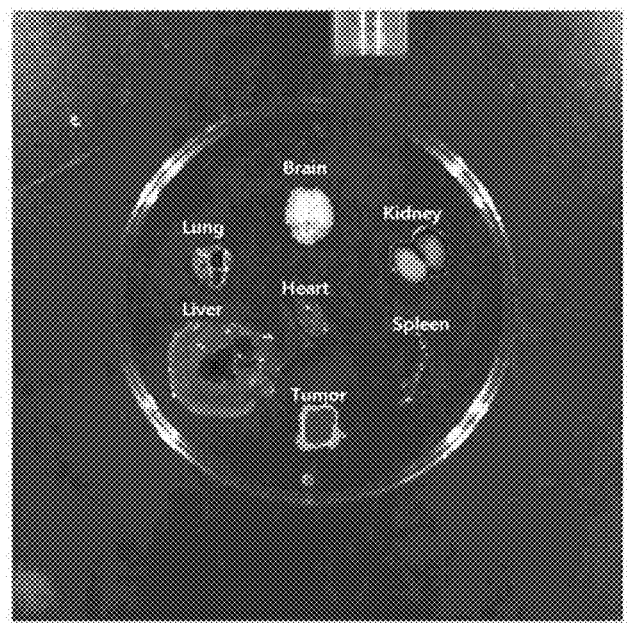

[Fig. 8c]
L-Triangular Prism (L-TP) – *ex vivo* (5 h)
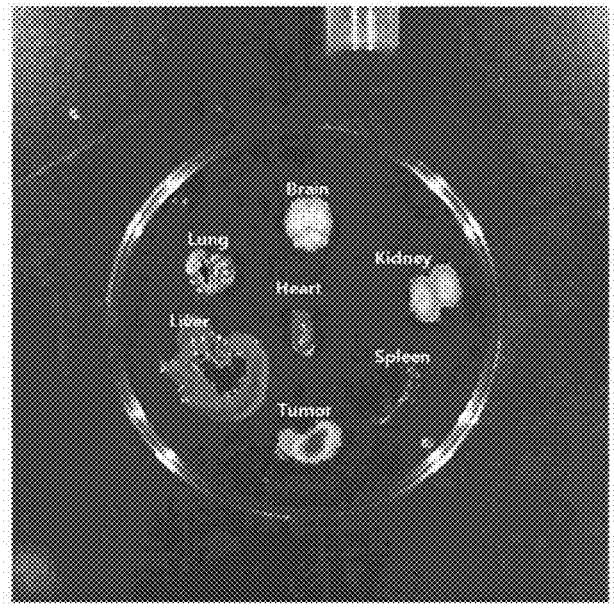
[Fig. 8d]
L-Cube (L-Cb) – *ex vivo* (4 h)
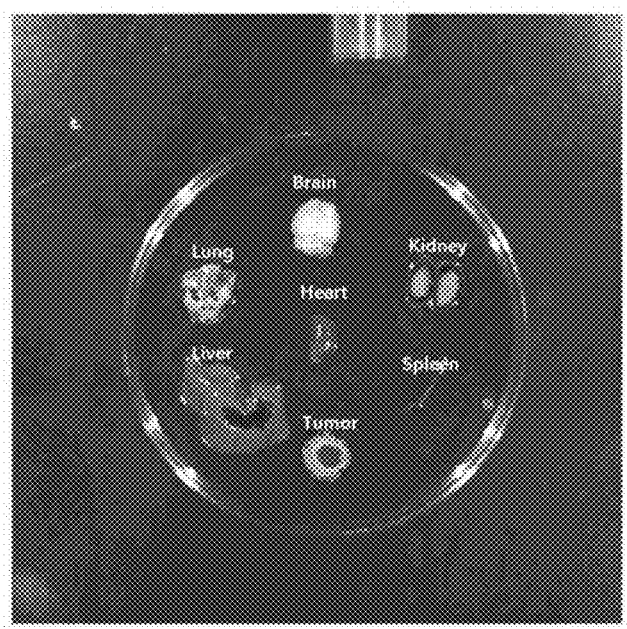

[Fig. 8e]
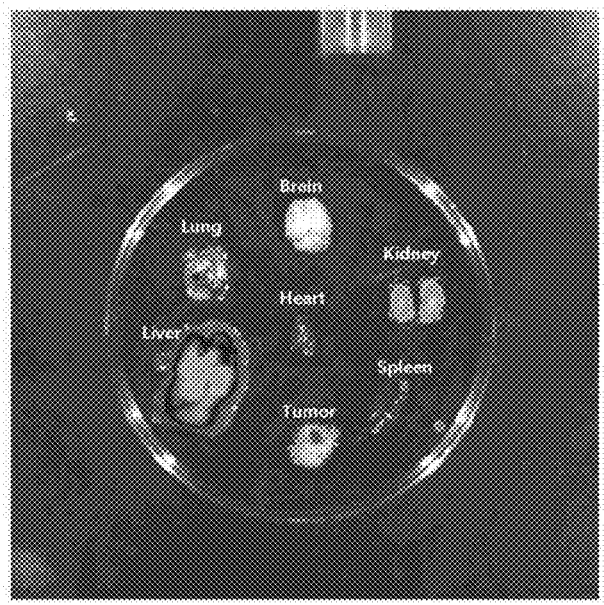

[Fig. 8f]
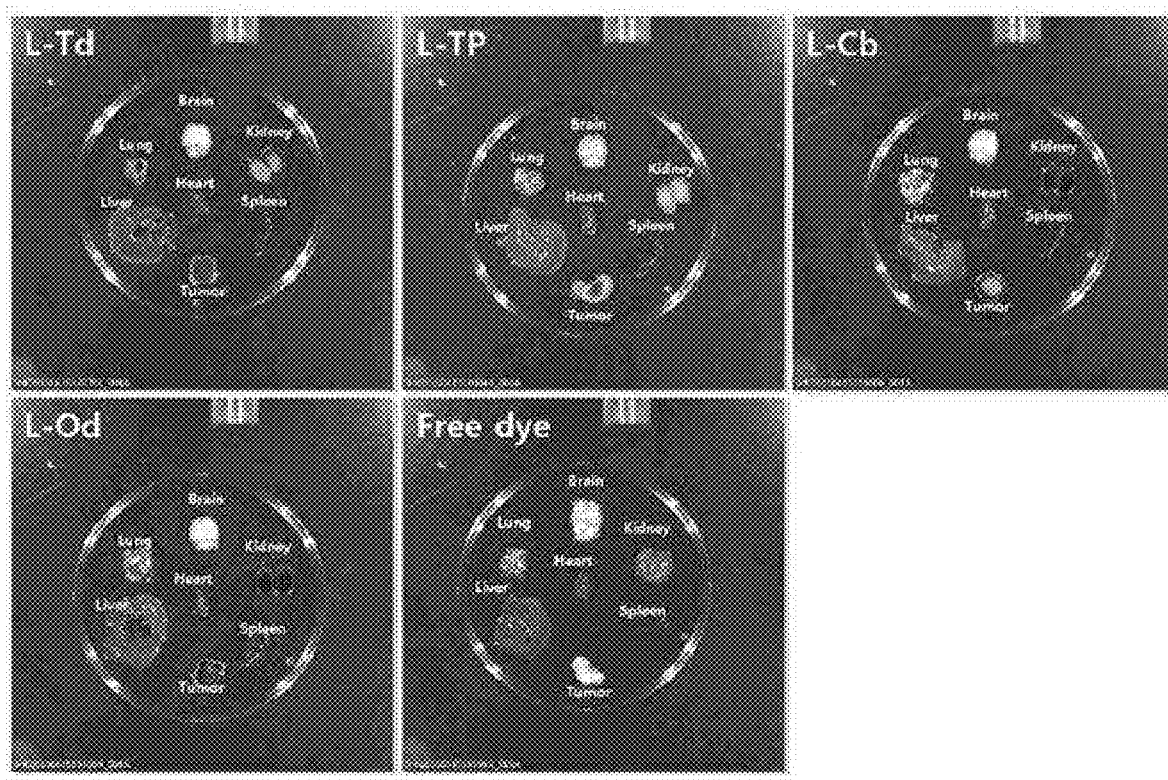

[Fig. 9a]
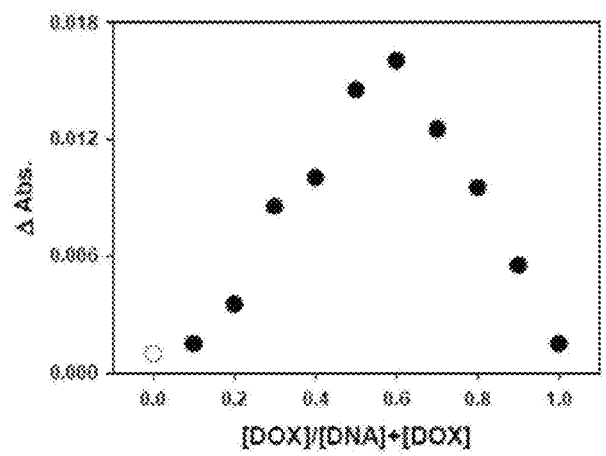
[Fig. 9b]
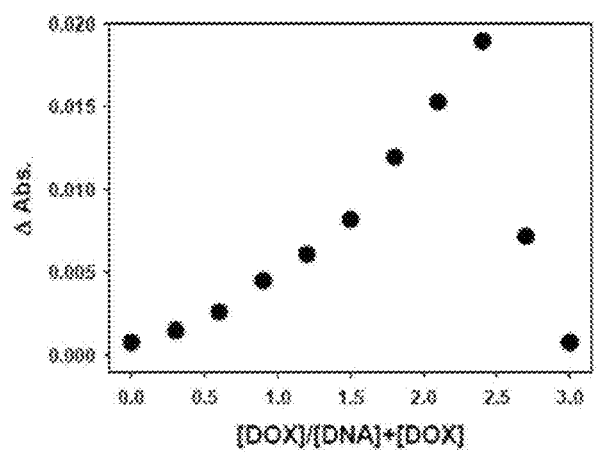

[Fig. 10]
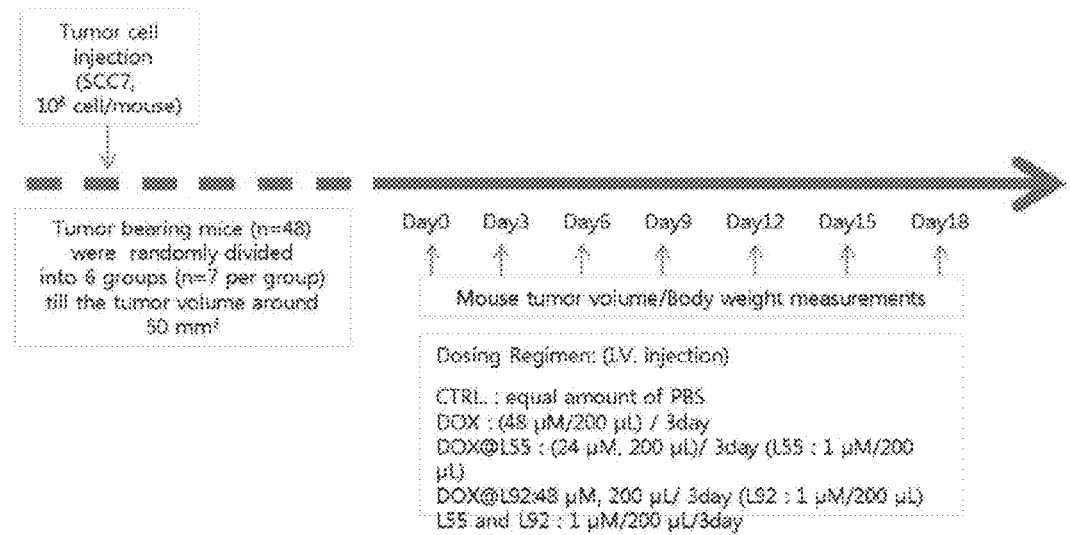
[Fig. 11]
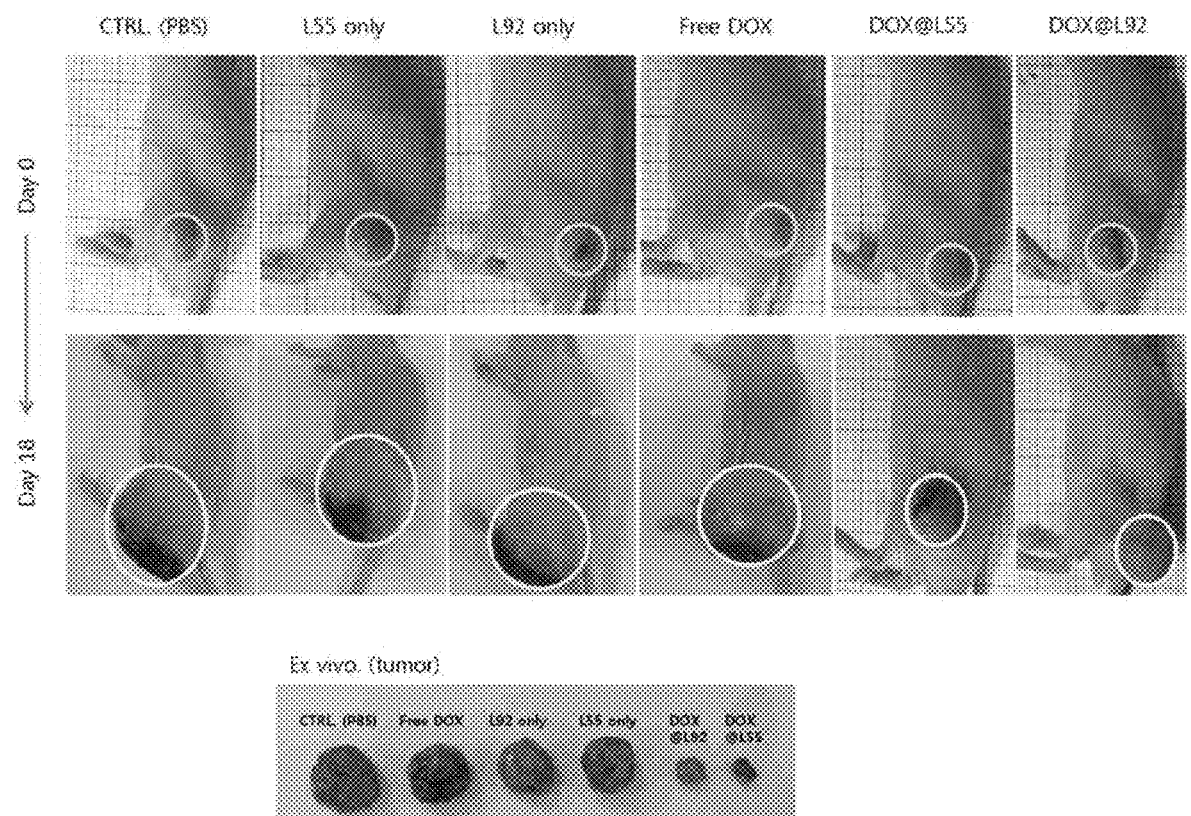

[Fig. 12a]
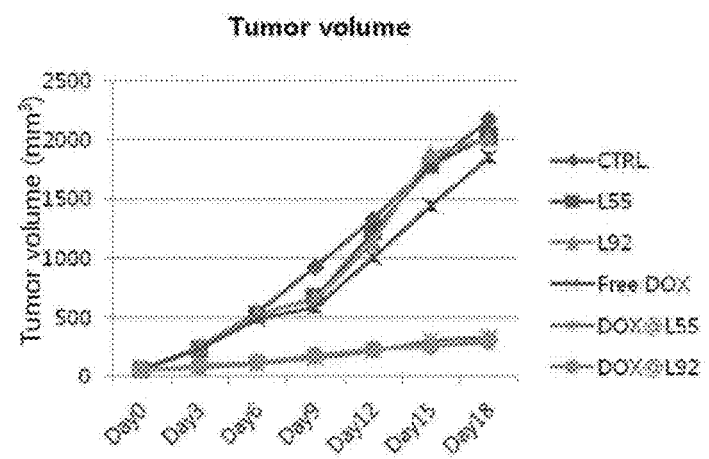
[Fig. 12b]
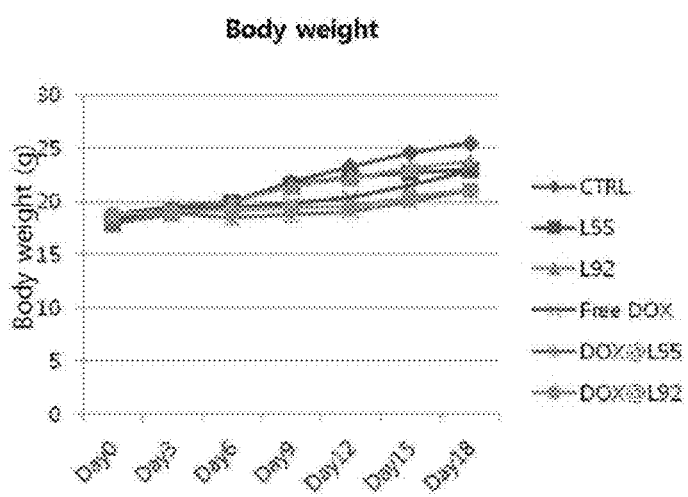

[Fig. 12c]
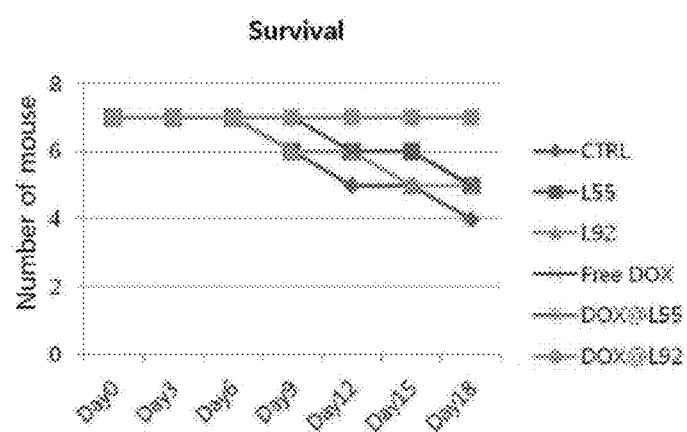
[Fig. 12d]
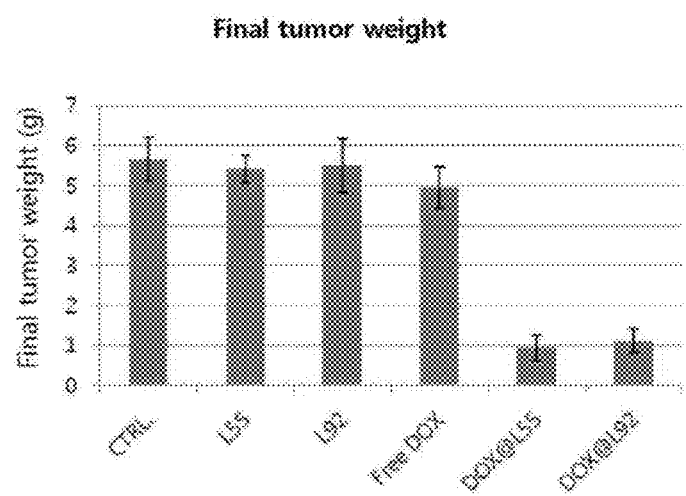

[Fig. 13]
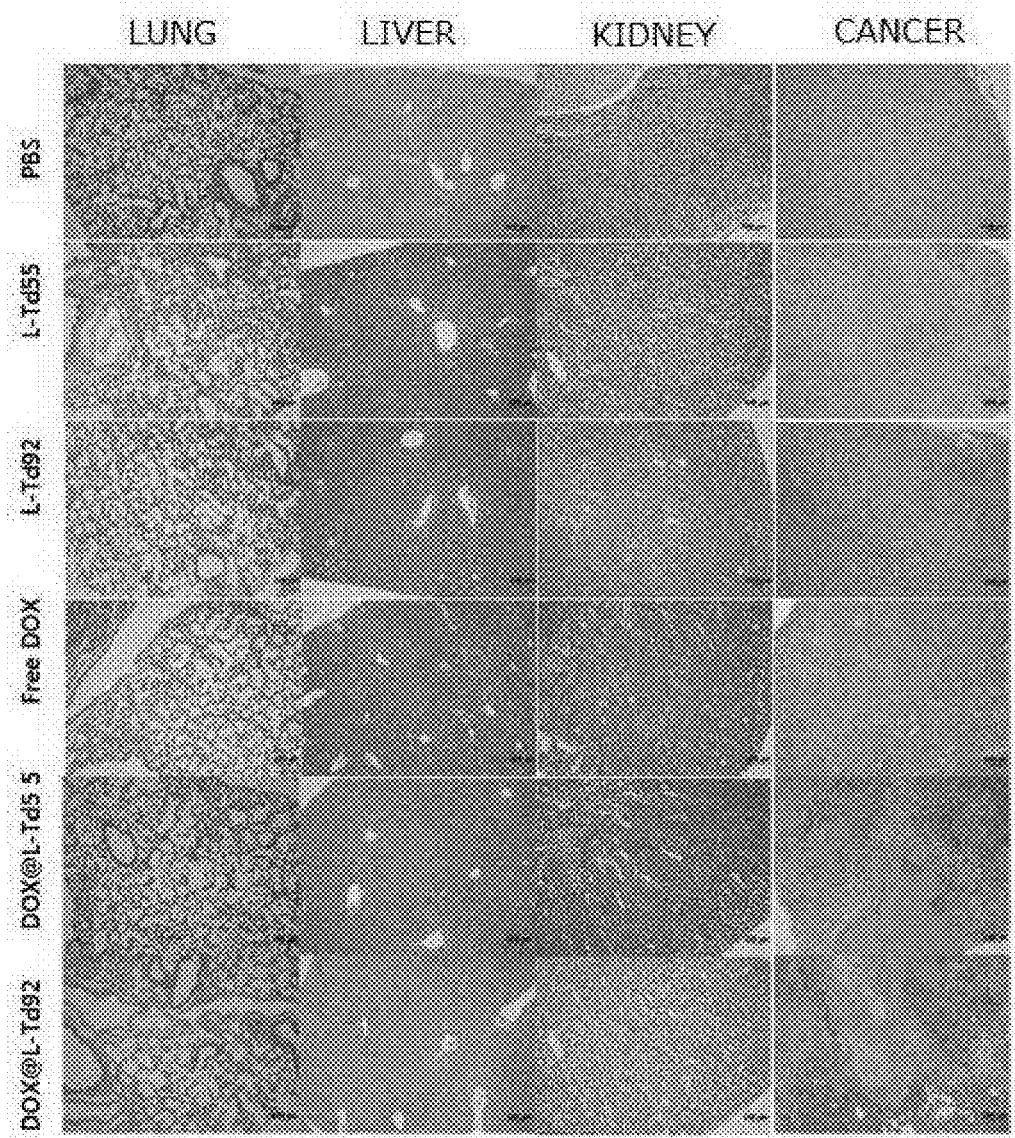

SEQUENCE LISTING

```
<160> NUMBER OF SEQ ID NOS: 33

<210> SEQ ID NO 1
<211> LENGTH: 55
<212> TYPE: DNA
<213> ORGANISM: Artificial Sequence
<220> FEATURE:
<223> OTHER INFORMATION: D/L 55_S1 oligonucleotide for D-DNA/L-DNA
<220> FEATURE:
<221> NAME/KEY: misc_feature
<222> LOCATION: (55)
<223> OTHER INFORMATION: Cy5.5-labeled

<400> SEQUENCE: 1
acattcctaa gtctgaaaca ttacagcttg ctacacgaga agagccgcca tagta          55

<210> SEQ ID NO 2
<211> LENGTH: 55
<212> TYPE: DNA
<213> ORGANISM: Artificial Sequence
<220> FEATURE:
<223> OTHER INFORMATION: D/L 55_S1 oligonucleotide for D-DNA/L-DNA
<220> FEATURE:
<221> NAME/KEY: misc_feature
<222> LOCATION: (55)
<223> OTHER INFORMATION: fluorescein-labeled

<400> SEQUENCE: 2
acattcctaa gtctgaaaca ttacagcttg ctacacgaga agagccgcca tagta          55

<210> SEQ ID NO 3
<211> LENGTH: 55
<212> TYPE: DNA
```

-continued

```
<213> ORGANISM: Artificial Sequence
<220> FEATURE:
<223> OTHER INFORMATION: D/L 55_S2 oligonucleotide for D-DNA/L-DNA

<400> SEQUENCE: 3
tatcaccagg cagttgacag tgtagcaagc tgtaatagat gcgagggtcc aatac        55

<210> SEQ ID NO 4
<211> LENGTH: 55
<212> TYPE: DNA
<213> ORGANISM: Artificial Sequence
<220> FEATURE:
<223> OTHER INFORMATION: D/L 55_S3 oligonucleotide for D-DNA/L-DNA

<400> SEQUENCE: 4
tcaactgcct ggtgataaaa cgacactacg tgggaatcta ctatggcggc tcttc        55

<210> SEQ ID NO 5
<211> LENGTH: 55
<212> TYPE: DNA
<213> ORGANISM: Artificial Sequence
<220> FEATURE:
<223> OTHER INFORMATION: D/L 55_S4 oligonucleotide for D-DNA/L-DNA

<400> SEQUENCE: 5
ttcagactta ggaatgtgct tcccacgtag tgtcgtttgt attggaccct cgcat        55

<210> SEQ ID NO 6
<211> LENGTH: 92
<212> TYPE: DNA
<213> ORGANISM: Artificial Sequence
<220> FEATURE:
<223> OTHER INFORMATION: D/L 92_S1 oligonucleotide for D-DNA/L-DNA
<220> FEATURE:
<221> NAME/KEY: misc_feature
<222> LOCATION: (92)
<223> OTHER INFORMATION: Cy5.5-labeled

<400> SEQUENCE: 6
ctcaactgcc tcagacggac aggtgatacg agagccggat gggcatgctc ttcccgtaga   60
gatagtacgg tattggaccg agtcctcgca tg                                 92

<210> SEQ ID NO 7
<211> LENGTH: 92
<212> TYPE: DNA
<213> ORGANISM: Artificial Sequence
<220> FEATURE:
<223> OTHER INFORMATION: D/L 92_S1 oligonucleotide for D-DNA/L-DNA
<220> FEATURE:
<221> NAME/KEY: misc_feature
<222> LOCATION: (92)
<223> OTHER INFORMATION: fluorescein-labeled

<400> SEQUENCE: 7
ctcaactgcc tcagacggac aggtgatacg agagccggat gggcatgctc ttcccgtaga   60
gatagtacgg tattggaccg agtcctcgca tg                                 92

<210> SEQ ID NO 8
<211> LENGTH: 92
<212> TYPE: DNA
<213> ORGANISM: Artificial Sequence
<220> FEATURE:
<223> OTHER INFORMATION: D/L 92_S2 oligonucleotide for D-DNA/L-DNA

<400> SEQUENCE: 8
cgtatcacct gtccgtctga ggcagttgag agatctcgaa cattcctaag tctgaagatc   60
```
catttatcac cagctgctgc acgccatagt ag                                    92

<210> SEQ ID NO 9
<211> LENGTH: 92
<212> TYPE: DNA
<213> ORGANISM: Artificial Sequence
<220> FEATURE:
<223> OTHER INFORMATION: D/L 92_S3 oligonucleotide for D-DNA/L-DNA

<400> SEQUENCE: 9
ggatcttcag acttaggaat gttcgagatc acatgcgagg actcggtcca ataccgtact     60
aacgattaca gatcaaagct acttgctaca cg                                    92

<210> SEQ ID NO 10
<211> LENGTH: 92
<212> TYPE: DNA
<213> ORGANISM: Artificial Sequence
<220> FEATURE:
<223> OTHER INFORMATION: D/L 92_S4 oligonucleotide for D-DNA/L-DNA

<400> SEQUENCE: 10
ctctacggga agagcatgcc catccggctc actactatgg cgtgcagcag ctggtgataa     60
aacgtgtagc aagtagcttt gatctgtaat cg                                    92

<210> SEQ ID NO 11
<211> LENGTH: 54
<212> TYPE: DNA
<213> ORGANISM: Artificial Sequence
<220> FEATURE:
<223> OTHER INFORMATION: Tetrahedron(L-Td) S1 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 11
cgatgtctaa gctgaccggg accgtgattc catgaccttta gagttgccac cagg           54

<210> SEQ ID NO 12
<211> LENGTH: 54
<212> TYPE: DNA
<213> ORGANISM: Artificial Sequence
<220> FEATURE:
<223> OTHER INFORMATION: Tetrahedron(L-Td) S2 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 12
gtcatggaat cacggtccgg ctcacattgg ctacagctat ccgatcgagg catg            54

<210> SEQ ID NO 13
<211> LENGTH: 54
<212> TYPE: DNA
<213> ORGANISM: Artificial Sequence
<220> FEATURE:
<223> OTHER INFORMATION: Tetrahedron(L-Td) S3 oligonucleotide
<220> FEATURE:

```
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 13
catgcctcga tcggatagcg gtcagcttag acatcggcaa gtgctgcgtc atac          54

<210> SEQ ID NO 14
<211> LENGTH: 54
<212> TYPE: DNA
<213> ORGANISM: Artificial Sequence
<220> FEATURE:
<223> OTHER INFORMATION: Tetrahedron(L-Td) S4 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 14
cctggtggca actctaaggt atgacgcagc acttgcctgt agccaatgtg agcc          54

<210> SEQ ID NO 15
<211> LENGTH: 72
<212> TYPE: DNA
<213> ORGANISM: Artificial Sequence
<220> FEATURE:
<223> OTHER INFORMATION: Triangular prism(L-TP) S1 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 15
cgatgtctaa gctgaccggg accgtgattc catgaccttac gagttgccac cagggaatcc   60
tatgctcgga cg                                                        72

<210> SEQ ID NO 16
<211> LENGTH: 72
<212> TYPE: DNA
<213> ORGANISM: Artificial Sequence
<220> FEATURE:
<223> OTHER INFORMATION: Triangular prism(L-TP) S2 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 16
```
cggtcagctt agacatcggg ctcacattgg ctacagctat ccgatcgagg catgcatact    60
gagagcgttc cg    72

<210> SEQ ID NO 17
<211> LENGTH: 72
<212> TYPE: DNA
<213> ORGANISM: Artificial Sequence
<220> FEATURE:
<223> OTHER INFORMATION: Triangular prism(L-TP) S3 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 17
cctggtggca actctaaggc gtatctgaac tgcgaccatg cctcgatcgg atagccaccg    60
aatggtgtat cg    72

<210> SEQ ID NO 18
<211> LENGTH: 54
<212> TYPE: DNA
<213> ORGANISM: Artificial Sequence
<220> FEATURE:
<223> OTHER INFORMATION: Triangular prism(L-TP) S4 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 18
ctgtagccaa tgtgagcccg tccgagcata ggattccgat acaccattcg gtgg    54

<210> SEQ ID NO 19
<211> LENGTH: 54
<212> TYPE: DNA
<213> ORGANISM: Artificial Sequence
<220> FEATURE:
<223> OTHER INFORMATION: Triangular prism(L-TP) S5 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 19
gtcgcagttc agatacgcgt catggaatca cggtcccgga acgctctcag tatg    54

<210> SEQ ID NO 20
<211> LENGTH: 72
<212> TYPE: DNA
<213> ORGANISM: Artificial Sequence
<220> FEATURE:
<223> OTHER INFORMATION: Cube(L-Cb) S1 oligonucleotide
<220> FEATURE:

```
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 20
cgatgtctaa gctgaccggg accgtgattc catgaccttta gagttgccac cagggaatcc    60
tatgctcgga cg                                                         72

<210> SEQ ID NO 21
<211> LENGTH: 72
<212> TYPE: DNA
<213> ORGANISM: Artificial Sequence
<220> FEATURE:
<223> OTHER INFORMATION: Cube(L-Cb) S2 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 21
cctggtggca actctaaggg ctcacattgg ctacagctat ccgatcgagg catgcatact    60
gagagcgttc cg                                                         72

<210> SEQ ID NO 22
<211> LENGTH: 72
<212> TYPE: DNA
<213> ORGANISM: Artificial Sequence
<220> FEATURE:
<223> OTHER INFORMATION: Cube(L-Cb) S3 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 22
catgcctcga tcggataggc gtatctgaac tgcgacgcaa gtgctgcgtc atacccaccg    60
aatggtgtat cg                                                         72

<210> SEQ ID NO 23
<211> LENGTH: 72
<212> TYPE: DNA
<213> ORGANISM: Artificial Sequence
<220> FEATURE:
<223> OTHER INFORMATION: Cube(L-Cb) S4 oligonucleotide
<220> FEATURE:
<221> NAME/KEY: misc_feature
```

<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 23
ggcattgtac cgtaaccgcg gtcagcttag acatcgcgca agacgttagt gtccgtatga    60
cgcagcactt gc                                                       72

<210> SEQ ID NO 24
<211> LENGTH: 72
<212> TYPE: DNA
<213> ORGANISM: Artificial Sequence
<220> FEATURE:
<223> OTHER INFORMATION: Cube(L-Cb) S5 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 24
gtcatggaat cacggtcccg gttacggtac aatgccgtcg cagttcagat acgcctgtag    60
ccaatgtgag cc                                                       72

<210> SEQ ID NO 25
<211> LENGTH: 72
<212> TYPE: DNA
<213> ORGANISM: Artificial Sequence
<220> FEATURE:
<223> OTHER INFORMATION: Cube(L-Cb) S6 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion
<220> FEATURE:
<221> NAME/KEY: misc_feature
<222> LOCATION: (54)..(55)
<223> OTHER INFORMATION: iSp (internal spacer) 18 insertion

<400> SEQUENCE: 25
ggacactaac gtcttgcgcg tccgagcata ggattccgga acgctctcag tatgcgatac    60
accattcggt gg                                                       72

<210> SEQ ID NO 26
<211> LENGTH: 54
<212> TYPE: DNA
<213> ORGANISM: Artificial Sequence
<220> FEATURE:
<223> OTHER INFORMATION: Octahedron(L-Od) S1 oligonucleotide
<220> FEATURE:
<221> NAME/KEY: misc_feature
<222> LOCATION: (18)..(19)

<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 26
cgatgtctaa gctgaccggg accgtgattc catgaccta gagttgccac cagg         54

<210> SEQ ID NO 27
<211> LENGTH: 54
<212> TYPE: DNA
<213> ORGANISM: Artificial Sequence
<220> FEATURE:
<223> OTHER INFORMATION: Octahedron(L-Od) S2 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 27
gtcatggaat cacggtccgg ctcacattgg ctacagctat ccgatcgagg catg         54

<210> SEQ ID NO 28
<211> LENGTH: 54
<212> TYPE: DNA
<213> ORGANISM: Artificial Sequence
<220> FEATURE:
<223> OTHER INFORMATION: Octahedron(L-Od) S3 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 28
ctgtagccaa tgtgagccgc gtatctgaac tgcgacgcaa gtgctgcgtc atac         54

<210> SEQ ID NO 29
<211> LENGTH: 54
<212> TYPE: DNA
<213> ORGANISM: Artificial Sequence
<220> FEATURE:
<223> OTHER INFORMATION: Octahedron(L-Od) S4 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 29
gtcgcagttc agatacgccg gtcagcttag acatcgcgca agacgttagt gtcc         54

<210> SEQ ID NO 30
<211> LENGTH: 54
<212> TYPE: DNA
<213> ORGANISM: Artificial Sequence
<220> FEATURE:
<223> OTHER INFORMATION: Octahedron(L-Od) S5 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 30
gaatcctatg ctcggacgca tactgagagc gttccgcctg gtggcaactc taag    54

<210> SEQ ID NO 31
<211> LENGTH: 54
<212> TYPE: DNA
<213> ORGANISM: Artificial Sequence
<220> FEATURE:
<223> OTHER INFORMATION: Octahedron(L-Od) S6 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 31
ccaccgaatg gtgtatcgcg tccgagcata ggattccatg cctcgatcgg atag    54

<210> SEQ ID NO 32
<211> LENGTH: 54
<212> TYPE: DNA
<213> ORGANISM: Artificial Sequence
<220> FEATURE:
<223> OTHER INFORMATION: Octahedron(L-Od) S7 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 32
ggcattgtac cgtaaccgcg atacaccatt cggtgggtat gacgcagcac ttgc    54

<210> SEQ ID NO 33
<211> LENGTH: 54
<212> TYPE: DNA
<213> ORGANISM: Artificial Sequence
<220> FEATURE:
<223> OTHER INFORMATION: Octahedron(L-Od) S8 oligonucleotide
<220> FEATURE:
<221> NAME/KEY: misc_feature
<222> LOCATION: (18)..(19)
<223> OTHER INFORMATION: iSp (internal spacer) 18 insertion
<220> FEATURE:
<221> NAME/KEY: misc_feature
<222> LOCATION: (36)..(37)
<223> OTHER INFORMATION: iSp (internal spacer) 18 insertion

<400> SEQUENCE: 33
cggaacgctc tcagtatgcg gttacggtac aatgccggac actaacgtct tgcg    54

DRUG CARRIER HAVING SELF-ASSEMBLED 3-D NUCLEIC ACID NANOSTRUCTURE

CROSS-REFERENCE TO RELATED APPLICATION

This application claims priority from Korean Patent Application No. 10-2014-0093458, filed on Jul. 23, 2014, contents of which are incorporated by reference herein in its entirety.

BACKGROUND OF INVENTION

1. Field of Invention

The present invention relates to a molecule delivery technology and a carrier technology, which can selectively deliver a material to a desired specific cell and living tissue.

The field for which the technology of the present invention may be utilized is largely the field of a drug carrier which effectively delivers an imaging probe and a therapeutic agent to an affected part.

2. Background of Invention

Examples of the existing drug delivery technology include a liposome carrier, a polymer-based carrier, a peptide carrier, and the like. However, the liposome carrier has low vesicle stability, relatively low drug-encapsulation rate and limited size reproducibility, and the polymer-based carrier is disadvantageous in that it has low biodegradability and limited size reproducibility, its in vivo drug metabolism is unclear, as well as it shows immunogenicity. The peptide carrier is also disadvantageous in having low thermal stability, and limited modification possibility and immunogenicity.

On the other hand, unlike the existing carriers, a carrier composed of nucleic acids is advantageous in that it is completely biodegradable into non-toxic small molecules, the size and shape thereof can be easily adjusted to a suitable level, it can be self-assembled and has monodispersity and non-immunogenicity, as well as it can be easily conjugated with functional molecules. Accordingly, DNA nanocarriers are an emerging class in drug delivery technologies.

Previously, it has been shown that biocompatible DNA could self-assemble to construct various three dimensional (3D) DNA nanostructures including tetrahedron, pentahedron, cube, double pyramid, octahedron, dodecahedron, and fullerene-like structures. Among them, the DNA tetrahedron has been considered one of the most practical DNA nanostructures since it can be assembled simply from four DNA strands and prepared in high yield. A principle in which the DNA tetrahedron is assembled from 4 DNA strands is by mutual hybridization, and a schematic view explaining the principle is illustrated in FIG. 1.

A recent report in which DNA nanostructures are taken up into mammalian cells has opened an opportunity that the nanostructures may serve an important role in being applied to biomedicine. They are often introduced into mammalian cells even without transfection agents. Further, it is known that DNA nanostructures are significantly resistant to nucleases.

Due to these characteristics, recently, DNA nanostructures have been utilized in intracellular delivery of bioactive molecules such as anticancer agents, aptamers, antisenses, immunogenic molecules, and siRNA.

Throughout the present specification, a plurality of documents are referenced, and citations thereof are indicated. The disclosure of each of the cited documents is incorporated herein by reference in its entirety to describe the level of the technical field to which the present invention pertains and the content of the present invention more apparently.

SUMMARY OF INVENTION

The present inventors have studied and tried to develop a drug carrier for systemic administration, which may specifically deliver a pharmaceutically active ingredient only to a specific tissue by in vivo administration. As a result, the present inventors have found that a self-assembled 3-D nucleic acid nanostructure not only has specificity for specific cells and tissues, but also can be specifically delivered only to the corresponding tissue by in vivo administration, particularly without targeting ligands, thereby completing the present invention.

Accordingly, an object of the present invention is to provide a self-assembled 3-D nucleic acid nanoparticle having selectivity for specific tissues to cells.

Another object of the present invention is to provide a drug carrier for systemic administration having the nucleic acid nanostructure, which is specific for a specific tissue.

The other objects and advantages of the present invention will be more apparent from the following detailed description, claims and drawings of the invention.

An aspect of the present invention is to provide a method of in vivo delivering a pharmaceutically active ingredient to a specific tissue, using a self-assembled 3-D nucleic acid nanostructure as a drug carrier.

In the method of present invention, the 3-D nucleic acid nanostructure drug carrier can deliver a pharmaceutically active ingredient specifically only to a target tissue by in vivo administration, and has cell or tissue specificity particularly without targeting ligands.

In order to specifically deliver nucleic acid to a specific cell such as a tumor cell in the related art, there has been an attempt to deliver nucleic acid using a ligand such as antibody or folate. However, it was impossible to achieve in vivo targeting without an additional process of binding the ligand, and also there was a problem that the ligand could cause an immune reaction and the like in an organism.

Under these circumstances, the present inventors provide an in vivo drug delivery technology in which only a target tissue is specifically targeted by administration of nucleic acid nanostructures only which are completely biodegraded into non-toxic small molecules in the organism.

In an exemplary embodiment, a drug carrier of the present invention has an L-DNA nanostructure, and has in vivo cancer tissue specificity.

The L-DNA nanoparticle may have various polyhedron structures such as, for example, a tetrahedron, a pentahedron, a cube, an octahedron, a dodecahedron, a cuboctahedron, and a dodecicosahedron, a double pyramid or fullerene structure, and the like, but is not necessarily limited thereto, and may preferably have a tetrahedron structure composed of 4 strands of L-DNA 55 mer or 4 strands of L-DNA 92 mer, but is not necessarily limited thereto.

The L-DNA polyhedron structure may be formed when a plurality of single stranded nucleic acid molecules, for example, 4 to 100, 4 to 50, or 4 to 20 stranded nucleic acid molecules are self-assembled by a hybridization principle.

In another exemplary embodiment, the drug carrier of the present invention has a D-DNA nanostructure, and has specificity for liver, skin, or kidney tissue during in vivo administration.

The carrier preferably may have in vivo liver tissue specificity as a tetrahedron nanostructure composed of 4 strands of D-DNA 55 mer, or have in vivo kidney tissue specificity as a tetrahedron nanostructure composed of 4 strands of D-DNA 92 mer, but is not necessarily limited thereto.

Meanwhile, a pharmaceutically active ingredient to be delivered specifically to an organism tissue or cell by the drug carrier of the present invention may be delivered while being encapsulated in a nucleic acid nanoparticle having a polyhedron structure of the present invention, or may also be delivered while being bonded to the backbone of nucleic acid.

The pharmaceutically active ingredient may be encapsulated in a polyhedron structure, or be allowed to be bonded to the backbone of nucleic acid by an action in which linear nucleic acid strands are assembled into a 3-D polyhedron nanostructure, for example, in a state where the linear nucleic strands are mixed with the active ingredient.

The pharmaceutically active ingredient, which may be delivered into cells using the drug carrier of the present invention, is not limited to a specific kind of ingredient, and examples thereof include an anticancer agent, a contrast medium, a hormone drug, an anti-hormone drug, a vitamin preparation, a calcium agent, an inorganic preparation, a sugar preparation, an organic acid preparation, a protein amino acid preparation, an antidote, an enzyme preparation, a metabolic preparation, a diabetes combination drug, a drug for tissue repair, a chlorophyll preparation, a pigment preparation, a tumor drug, a tumor therapeutic agent, a radioactive medicine, a tissue cell diagnostic agent, a tissue cell therapeutic agent, an antibiotic preparation, an antiviral drug, a complex antibiotic preparation, a chemotherapeutic agent, a vaccine, a toxin, a toxoid, an antitoxin, leptospira serum, a blood preparation, a biological preparation, an analgesic, an immunogenic molecule, an antihistamine, an allergy drug, a non-specific immunogenic preparation, an anesthetic, an antihypnotic, a neuropsychiatric solvent, nucleic acid, an aptamer, an antisense nucleic acid, an oligonucleotide, peptide, siRNA, micro RNA, and the like, but are not necessarily limited thereto.

Another aspect of the present invention relates to a method of in vivo delivering an anticancer agent specifically to cancer cells, comprising administering a pharmaceutical composition including the aforementioned 3-D nucleic acid nanostructure drug carrier and an anticancer agent.

According to an exemplary embodiment of the present invention, the anticancer agent may be encapsulated in the nucleic acid drug carrier of the present invention or be bonded to the backbone of nucleic acid, and examples of the anticancer which may be used include doxorubicin, DNA aptamer, RNA aptamer, acivicin, aclarubicin, acodazole, acronycine, adozelesin, alanosine, aldesleukin, allopurinol sodium, altretamine, aminoglutethimide, amonafide, ampl igen, amsacrine, androgens, anguidine, aphidicolin glycinate, asaley, asparaginase, 5-azacitidine, azathioprine, *Bacillus calmette-guerin* (BCG), Baker's Antifol, beta-2-deoxythioguanosine, bisantrene HCl, bleomycin sulfate, busulfan, buthionine sulfoximine, BWA 773U82, BW 502U83/HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabismaleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, echinomycin, dedatrexate, edelfosine, eplolnitin, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alpha, interferon beta, interferon gamma, interleukin-I alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extract of *Bacillus calmette-guerin*, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, mixtures thereof, and the like, but are not necessarily limited thereto.

The pharmaceutical composition may further include a pharmaceutically acceptable carrier, and the pharmaceutically acceptable earner is typically used in formulations and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto. Suitable pharmaceutically acceptable carriers and formulations are described in detail in *Remington's Pharmaceutical Sciences* (19th ed., 1995).

In the method of present invention, the pharmaceutical composition 1s systemically administered, and may be administered parenterally or orally. In case of parenteral administration, it may be administered through intravenous injection, intramuscular injection, and the like. An adequate administration amount of the pharmaceutical composition of the present invention may vary depending on factors, such as formulation method, administration method, age, weight, sex or disease condition of the patient, diet, administration time, administration route, elimination rate and response sensitivity.

Still another aspect of the present invention provides a method of in vivo delivering a contrast medium to a specific tissue for imaging, comprising administering a pharmaceutical composition including the aforementioned 3-D nucleic acid nanostructure drug carrier and a contrast medium.

In an exemplary embodiment, an inorganic or organic dye, a fluorescent substance, an isotope, a magnetic substance, a paramagnetic or superparamagnetic nanoparticle may be used as the contrast medium.

Herein, the inorganic or organic dyes are used for enhancing image contrast in fluorescent or optical image, radiation imaging such as computed tomography (CT) photography, and non-radiation image such as sonogram or MRI including the existing dyes, and may include, for example, diatrizoate, metrizoate, ioxaglate, iopamidol, iohexyl, ioxilan, iopromide, iodixanol, barium-based dye such as barium sulfate, Gastrografin®, and the like, but are not necessarily limited thereto.

The fluorescent probe may include, for example, indocyanine, NIR (near infrared) dye, fluorescein, phycoerythrin, rhodamine, lissamine, Cy3, Cy5 (Pharmacia), chromophore, chemical luminophore, mass labeling, electron dense particle, enzymes (alkaline phosphatase or horseradish peroxidase), but is not necessarily limited thereto.

In the contrast medium composition of the present invention, the composition may be a magnetic substance, and a paramagnetic or superparamagnetic nanoparticle, and in this case, may be usefully utilized particularly in imaging using MRI.

The paramagnetic nanoparticle is a material which may induce spin-lattice relaxation, and it is possible to use, for example, Magnevist (Schering, Germany), Gd chelating compounds such as Gd-DTPA (Gd-diethylene triamine pentaacetic acid), and a material such as $Gd_2O_3$ (C. Riviere et al. J. Am. Chem. Soc. 2007, 129, 5076.) and MnO (T. Hyeon et al. Angew. Chem. Int. Ed. 2007, 46, 5397.).

Further, the superparamagnetic nanoparticle is a material which is magnetized by an externally given magnetic field, affects the spin-spin process of a hydrogen nuclear spin in surrounding water molecules by generating an induced magnetic field, and shows a dark or negative contrast effect typically compared with water by amplifying the magnetic resonance imaging signal, and for example, Feridex, Resovist, Combidex, MEIO (magnetism engineered iron oxide) and the like including oxidized iron components.

As described above, depending on what contrast medium is encapsulated in the nucleic acid nanoparticle drug carrier having a polyhedron structure of the present invention or is bonded to the backbone of nucleic acid, the contrast medium composition of the present invention may be used appropriately for fluorescence imaging, optical imaging, radiation imaging, computed tomography (CT) photography or MRI.

In a preferred exemplary embodiment of the present invention, the contrast medium composition may be for imaging of liver, kidney, or cancer tissues.

The 3-D nucleic nanoparticle drug carrier of the present invention an in vivo drug delivery technology which targets only a specific tissue even without including a target ligand during the administration in an organism.

The drug carrier of the present invention as described above may be completely biodegraded into non-toxic small molecules, and the size and shape thereof may be easily adjusted to a suitable level, and the carrier is advantageous in being capable of being self-assembled while having monodispersity and non-immunogenicity, and being easily conjugated with functional molecules, and simultaneously has specific cell or biotissue selectivity. Accordingly, the drug carrier of the present invention may be usefully utilized as a drug carrier.

BRIEF DESCRIPTION OF THE DRAWINGS

The patent or application file contains at least one drawing executed in color. Copies of this patent or patent application publication with color drawing(s) will be provided by the office upon request and payment of the necessary fee.

1. FIG. 1 is a schematic view illustrating a principle in which a DNA polyhedron is assembled from 4 DNA strands by hybridization.

2. FIG. 2*a* is a schematic view illustrating a process in which a library of DNA nanostructures is prepared by changing the sugar backbone and size, and the cell and biotissue specificity thereof is confirmed, and FIG. 2*b* illustrates a result in which 4 DNA tetrahedrons (DSS, LSS, D92, and L92) are prepared and confirmed by PAGE.

3. FIGS. 3*a* to 3*d* illustrate the results in which cells transfected with 4 DNA tetrahedrons (DSS, LSS, D92, and L92) are observed through fluorescent microscopy (FIG. 3*a*: Hela cells, FIG. 3*b*: HepG2 cells, FIG. 3*c*: AS49 cells, and FIG. 3*d*: MCF7 cells).

4. FIG. 4 illustrates the results in which cells transfected with 4 DNA tetrahedrons (DSS, LSS, D92, and L92) are subjected to flow cytometry.

5. FIGS. 5*a* to 5*g* illustrates fluorescent images obtained by injecting 4 DNA polyhedrons (DSS, LSS, D92, and L92) into mice. Specifically, FIG. 5*a*: Fluorescent image obtained by injecting SS Td, FIG. 5*b*: Fluorescent image obtained by injecting D92 Td, FIG. 5*c*: Comparison of in vivo fluorescent images obtained by injecting LSS and L92 and leaving the mice to stand for 0 minute to 24 hours after the injection, FIG. 5*d*: Fluorescent image obtained by injecting LSS and leaving the mouse to stand for 0 minute to 5 hours (in vivo+ex vivo 5 hours after injection), FIG. 5*e*: Fluorescent image obtained by injecting L92 and leaving the mouse to stand for 0 minute to 7 hours (in vivo+ex vivo 7 hours after injection), FIG. 5*f*: Comparison of ex vivo fluorescent images obtained by injecting LSS and L92 (L55 and L92 are obtained 5 hours after injection and 7 hours after injection, respectively), and FIG. 5*g*: Comparison of ex vivo fluorescent images obtained by injecting L55 and L92 (after adjusting scale).

6. FIGS. 6*a* to 6*d* illustrate the results in which the formation of the 4 (L-Td, L-TP, L-Cb, and L-Od) structures are confirmed by PAGE (FIG. 6*a*: L-Td, FIG. 6*b*: L-TP, FIG. 6*c*: L-Cb, and FIG. 6*d*: L-Od).

7. FIGS. 7*a* to 7*f* illustrate the results in which L-DNA nanostructures fluorescently labeled are injected into a mouse tumor model, and a change in distribution of nanostructures in the organism is observed (FIG. 7*a*: Free dye, FIG. 7*b*: L-Td, FIG. 7*c*: L-TP, FIG. 7*d*: L-Cb, FIG. 7*e*: L-Od, and FIG. 7*f*: Comparison of in vivo images of 4 structures on the same scale).

8. FIGS. 8*a* to 8*f* illustrate the results in which L-DNA nanostructures fluorescently labeled are injected into a tumor model, the mouse was sacrificed, and 6 organs of brain, heart, lung, liver, kidney, and spleen and tumor were removed and observed (FIG. 8*a*: Free dye, FIG. 8*b*: L-Td, FIG. 8*c*: L-TP, FIG. 8*d*: L-Cb, FIG. 8*e*: L-Od, and FIG. 8*f*: Comparison of ex vivo images of 4 structures on the same scale).

9. FIGS. 9*a* and 9*b* illustrate the results in which an optimal binding ratio is searched using a Job plot in order to load a doxorubicin (DOX) drug into L-Td55 (FIG. 9*a*) and L-Td92 (FIG. 9*b*).

10. FIG. 10 illustrates a schematic view of selective DOX delivery and therapy of a cancer tissue using a Xenograft cancer mouse animal model.

11. FIG. 11 illustrates photographs of external parts of mice which were classified into total 6 groups (PBS, L-Td55, L-Td92, free DOX, DOX@L-Td55, and DOX@L-Td92) and treated for 18 days, and a photograph of tumors removed at the final day of therapy.

12. FIGS. 12(a-d) are graphs illustrating changes in mice which were classified into total 6 groups (PBS, L-Td55, L-Td92, free DOX, DOX@L-Td55, and DOX@L-Td92) and treated for 18 days during the therapy period (FIG. 12a: Change in volume of tumor, FIG. 12b: Change in body weight, FIG. 12c: Number of survived mice, and FIG. 12d: Final tumor weight).

13. FIG. 13. illustrates the results in which mice were classified into total 6 groups (PBS, L-Td55, L-Td92, free DOX, DOX@L-Td55, and DOX@L-Td92), treated for 18 days, and sacrificed at the final day of therapy, and lung, liver, kidney, and cancer removed were observed through optical microscopy.

DETAILED DESCRIPTION OF INVENTION

Hereinafter, the present invention will be described in more detail through the Examples. These Examples are provided only for more specifically describing the present invention, and it will be obvious to a person with ordinary skill in the art to which the present invention pertains that the scope of the present invention is not limited by these Examples.

EXAMPLES

I. In Vivo Biodistribution of D/L-DNA Nanostructures

1. Preparation of DNA Nanostructures Through Synthesis and Self-Assembly of D/L-DNA Oligonucleotides 13

DNA oligonucleotides required for the Tds structure were synthesized by using a DNA synthesis standard protocol. The base sequence of the 55mer DNA standard was adopted from the Tuberfield Td, and the base sequence of the 92mer DNA standard was adopted from the Anderson (Lee et al. Nat. Nanotechnol. 2012, 7, 389-393). The oligonucleotide sequences used to constitute total 4 DNA nanostructures (D-DNA 55mer Td, L-DNA 55mer Td, D-DNA 92mer Td, and L-DNA 92mer Td) are shown in the following Table 1.

TABLE 1

| | Sequence (5' to 3') | |
|---|---|---|
| Cy5.5-labeled D/L 55_S1 | ACATTCCTAAGTCTGAAACATTACAGCTTGC TACACGAGAAGAGCCGCCATAGTA-Cy5.5 | SEQ ID NO: 1 |
| Fluorescein-labeled D/L 55_S1 | ACATTCCTAAGTCTGAAACATTACAGCTTGC TACACGAGAAGAGCCGCCATAGTA-fluorescein | SEQ ID NO: 2 |
| D/L 55_S2 | TATCACCAGGCAGTTGACAGTGTAGCAAGC TGTAATAGATGCGAGGGTCCAATAC-NH$_2$ | SEQ ID NO: 3 |
| D/L 55_S3 | TCAACTGCCTGGTGATAAAACGACACTACGT GGAATCTACTATGGCGGCTCTTC-NH$_2$ | SEQ ID NO: 4 |
| D/L 55_S4 | TTCAGACTTAGGAATGTGCTTCCCACGTAG TGTCGTTTGTATTGGACCCTCGCAT-NH$_2$ | SEQ ID NO: 5 |
| Cy5.5-labeled D/L 92_S1 | CTCAACTGCCTCAGACGGACAGGTGATACGA GAGCCGGATGGGCATGCTCTTCCCGTAGAGA TAGTACGGTATTGGACCGAGTCCTCGCATG-Cy5.5 | SEQ ID NO: 6 |
| Fluorescein-labeled D/L 92_S1 | CTCAACTGCCTCAGACGGACAGGTGATACGA GCCGGATGGGCATGCTCTTCCCGTAGAGATG AAGTACGGTATTGGACCGAGTCCTCGCATG-fluorecein | SEQ ID NO: 7 |
| D/L 92_S2 | CGTATCACCTGTCCGTCTGAGGCAGTTGAGAG ATCTCGAACATTCCTAAGTCTGAAGATCCATT TATCACCAGCTGCTGCACGCCATAGTAG-NH$_2$ | SEQ ID NO: 8 |
| D/L 92_S3 | GGATCTTCAGACTTAGGAATGTTCGAGATCAC ATGCGAGGACTCGCTCCAATACCGTACTAACG ATTACAGATCAAAGCTACTTGCTACACG-NH$_2$ | SEQ ID NO: 9 |
| D/L 92_S4 | CTCTACGGGAAGAGCATGCCCATCCGGCTCAC TACTATGGCGTGCAGCAGCTGGTGATAAAACG TGTAGCAAGTAGCTTTGATCTGTAATCG-NH$_2$ | SEQ ID NO: 10 |

A library of DNA nanostructures was prepared by performing the Td assembly as described in the document (Kim et al. Chem. Sci., 2014, 5, 1533-1537) to change the sugar backbone and size (see FIG. 2a), and then the self-assembled D and L-Td (D-DNA 55mer Td, L-DNA 55mer Td, D-DNA 92mer Td, and L-DNA 92mer Td) were confirmed by performing 6% non-denaturing polyacrylamide gel electrophoresis (PAGE) (FIG. 2b).

2. Cell Selectivity of DNA Nanostructures (1) Transfection of DNA Nanostructures into HeLa, HepG2, A549 and MCF7 Cells In order to confirm the cell selectivity of each DNA nanostructure, cancer cells were treated with the DNA nanostructures prepared above.

Specifically, HeLa, HepG2, A549 and MCF7 cells were each inoculated into a glass-bottom 35-mm petri dish including a DMEM medium (Gibco, USA) containing 10% fetal bovine serum inactivated with heat, 1% penicillin, and streptomycin, and then the dish was cultured in a wet atmosphere including 5% CO2 at 37° C. The growth medium was removed from each cell sample and washed twice with PBS (Gibco, USA), and the DNA nanostructures prepared were subjected to transfection treatment in each cell.

(2) Microscopic Images of DNA Nanostructures in Cell

Cells transfected with the DNA nanostructures were observed under a fluorescent microscope (DeltaVision, Applied Precision, USA) and living cells were imaged, and the results are each shown in FIG. 3 (FIGS. 3a to 3d).

As a result of the experiment, it could be seen that the DNA nanostructures were entered into the cells, and it could be confirmed that the DNA nanostructures were in the cytoplasm region without being delivered to the cell nucleus.

(3) Flow Cytometry

The HeLa, HepG2, A549 and MCF7 cells were cultured with DNA molecules fluorescently labeled using the method which is the same as that adopted in the transfection experiment, the fluorescence intensity of the cells was evaluated using a flow cytometer (FC500, Beckman coulter, USA), and then, the result is shown in FIG. 4.

Based on the result that the amount of each nanostructure delivered into the cells was quantified through a flow cytometry, the amounts delivered for each cell could be compared with each other, and as a result of the experiment, it was confirmed that D55 had HepG2 cell selectivity, L55 simultaneously had strong HeLa cell selectivity and considerable HepG2 cell selectivity, and L92 had HeLa and HepG2 cell selectivity (FIG. 4).

As described above, since the kind of cell delivered in a large amount for each structure is present, it was confirmed that a structure having cell selectivity could be discovered through the construction of a library composed of various DNA nanostructures.

3. Tissue Selectivity of DNA Nanostructures (1) In Vivo Imaging

The animal experiment was approved by the Institutional Animal Care and Use Committee of Korean Institute of Science and Technology, and all the mice were treated according to the regulations of the committee. For in vivo imaging and establishment of a disease model, a mouse was anesthetized by intraperitoneally injecting 0.5% pentobarbital sodium (0.01 m L/g). An animal disease model was established by using a BALB/c nude mouse (5 weeks old, male, Orient Bio Inc., Korea). A tumor was produced by subcutaneously inoculating SCC7 cells ($1.0 \times 10^6$ cells suspended in a culture medium) into the thigh of the mouse.

The DNA structures prepared were injected into the caudal vein of the mouse, and fluorescent images obtained by using a CCD camera performed in a highly sensitive imaging system (IVIS-spectrum, Perkin-Elmer, USA) are shown in FIG. 5 (FIGS. 5a to 5e).

(2) Ex Vivo Imaging and Histological Analysis After an in vivo imaging study, ex vivo near-infrared fluorescence images for excised organs and the other sites of the body were obtained by using an IVIS-spectrum imaging system including the same obtaining set as that used for in vivo imaging, and the results are shown in FIG. 5 (the second photograph in FIGS. 5a and 5b, the last photograph in FIGS. 5d and 5e, FIG. 5f, and FIG. 5g).

As a result of the experiment, it was confirmed that D55 was delivered more selectively to the liver, and distributed even in the skin tissue. On the contrary, D92 was delivered more selectively to the kidney. It was shown that L55 and L92 were accumulated, exhibiting high selectivity for the cancer tissue In addition, it was observed that as time elapsed, L-Td's had accumulated been more selectively in cancer instead of being distributed throughout the tissue than D-Td (after about 6 to 7 hours), and had escaped after 24 hours.

II. Evaluation of In Vivo Biodistribution of L-DNA Nanostructures

1. Formation of Structure Labeled with Fluorescent Dye (1) Formation of 4 Structures (L-Td, L-TP, L-Cb, and L-Od)

The oligonucleotide sequences used to self-assemble total four L-DNA nanostructures having tetrahedron (L-Td), triangular prism (L-TP), cube (L-Cb) and octahedron (L-Od) shapes as an L-DNA nanostructure are shown in the following Tables 2 to 5.

TABLE 2

| Structure | | Sequence (5' to 3') | |
|---|---|---|---|
| Tetrahedron (L-Td) | S1 | CGATGTCTAAGCTGACCG/iSp18/GGAC CGTGATTCCATGAC/iSp18/CTTAGAGT TGCCACCAGG | SEQ ID NO: 11 |
| | S2 | GTCATGGAATCACGGTCC/iSp18/GGCT CACATTGGCTACAG/iSp18/CTATCCGA TCGAGGCATG | SEQ ID NO: 12 |
| | S3 | CATGCCTCGATCGGATAG/iSp18/CGG TCAGCTTAGACATCG/iSp18/GCAAGT GCTGCGTCATAC | SEQ ID NO: 13 |

TABLE 2-continued

| Structure | | Sequence (5' to 3') | |
|---|---|---|---|
| | S4 | CCTGGTGGCAACTCTAAG/iSp18/GTA TGACGCAGCACTTGC/iSp18/CTGTAG CCAATGTGAGCC | SEQ ID NO: 14 |

TABLE 3

| Structure | | Sequence (5' to 3') | |
|---|---|---|---|
| Triangular prism (L-TP) | S1 | CGATGTCTAAGCTGACCG/iSp18/ GGACCGTGATTCCATGAC/iSp18/ CTTAGAGTTGCCACCAGG/iSp18/ GAATCCTATGCTCGGACG | SEQ ID NO: 15 |
| | S2 | CGGTCAGCTTAGACATCG/iSp18/ GGCTCACATTGGCTACAG/iSp18/ CTATCCGATCGAGGCATG/iSp18/ CATACTGAGAGCGTTCCG | SEQ ID NO: 16 |
| | S3 | CCTGGTGGCAACTCTAAG/iSp18/ GCGTATCTGAACTGCGAC/iSp18/ CATGCCTCGATCGGATAG/iSp18/ CCACCGAATGGTGTATCG | SEQ ID NO: 17 |
| | S4 | CTGTAGCCAATGTGAGCC/iSp18/ CGTCCGAGCATAGGATTC/iSp18/ CGATACACCATTCGGTGG | SEQ ID NO: 18 |
| | S5 | GTCGCAGTTCAGATACGC/iSp18/ GTCATGGAATCACGGTCC/iSp18/ CGGAACGCTCTCAGTATG | SEQ ID NO: 19 |

TABLE 4

| Structure | | Sequence (5' to 3') | |
|---|---|---|---|
| Cube (L-Cb) | S1 | CGATGTCTAAGCTGACCG/iSp18/ GGACCGTGATTCCATGAC/iSp18/ CTTAGAGTTGCCACCAGG/iSp18/ GAATCCTATGCTCGGACG | SEQ ID NO: 20 |
| | S2 | CCTGGTGGCAACTCTAAG/iSp18/ GGCTCACATTGGCTACAG/iSp18/ CTATCCGATCGAGGCATG/iSp18/ CATACTGAGAGCGTTCCG | SEQ ID NO: 21 |
| | S3 | CATGCCTCGATCGGATAG/iSp18/ GCGTATCTGAACTGCGAC/iSp18/ GCAAGTGCTGCGTCATAC/iSp18/ CCACCGAATGGTGTATCG | SEQ ID NO: 22 |
| | S4 | GGCATTGTACCGTAACCG/iSp18/ CGGTCAGCTTAGACATCG/iSp18/ CGCAAGACGTTAGTGTCC/iSp18/ GTATGACGCAGCACTTGC | SEQ ID NO: 23 |
| | S5 | GTCATGGAATCACGGTCC/iSp18/ CGGTTACGGTACAATGCC/iSp18/ GTCGCAGTTCAGATACGC/iSp18/ CTGTAGCCAATGTGAGCC | SEQ ID NO: 24 |
| | S6 | GGACACTAACGTCTTGCC/iSp18/ CGTCCGAGCATAGGATTC/iSp18/ CGGAACGCTCTCAGTATG/iSp18/ CGATACACCATTCGGTGG | SEQ ID NO:25 |

TABLE 5

| Structure | | Sequence (5' to 3') | |
|---|---|---|---|
| Octahedron (L-Od) | S1 | CGATGTCTAAGCTGACCG/iSp18/ GGACCGTGATTCCATGAC/iSp18/ CTTAGAGTTGCCACCAGG | SEQ ID NO: 26 |
| | S2 | GTCATGGAATCACGGTCC/iSp18/ GGCTCACATTGGCTACAG/iSp18/ CTATCCGATCGAGGCATG | SEQ ID NO: 27 |
| | S3 | CTGTAGCCAATGTGAGCC/iSp18/ GCGTATCTGAACTGCGAC/iSp18/ GCAAGTGCTGCGTCATAC | SEQ ID NO: 28 |
| | S4 | GTCGCAGTTCAGATACGC/iSp18/ CGGTCAGCTTAGACATCG/iSp18/ CGCAAGACGTTAGTGTCC | SEQ. ID NO: 29 |
| | S5 | GAATCCTATGCTCGGACG/iSp18/ CATACTGAGAGCGTTCCG/iSp18/ CCTGGTGGCAACTCTAAG | SEQ ID NO: 30 |
| | S6 | CCACCGAATGGTGTATCG/iSp18/ CGTCCGAGCATAGGATTC/iSp18/ CATGCCTCGATCGGATAG | SEQ ID NO: 31 |
| | S7 | GGCATTGTACCGTAACCG/iSp18/ CGATACACCATTCGGTGG/iSp18/ GTATGACGCAGCACTTGC | SEQ ID NO: 32 |
| | S8 | CGGAACGCTCTCAGTATG/iSp18/ CGGTTACGGTACAATGCC/iSp18/ GGACACTAACGTCTTGCG | SEQ ID NO: 33 |

The strands constituting the structure were mixed so as to have a concentration of 1 μM based on each strand. In this case, a TM buffer (10 mM Tris-HCl, 5 mM $MgCl_2$, pH 8.0) was used as a buffer. The mixture was denatured through heating at 95° C. by using a RT-PCR machine, and was slowly cooled at 4° C. to be annealed.

As a result, it was confirmed by a non-denaturing PAGE that the resulting four (L-Td, L-TP, L-Cb, and L-Od) structures had been formed, and the results are each shown in FIGS. 6a to 6d (FIG. 6a: L-Td, FIG. 6b: L-TP, FIG. 6c: L-Cb, and FIG. 6d: L-Od).

(2) Labeling with Fluorescent Dye (Red Fluorescence)

A red fluorescent dye (SYTO® 62 Red Fluorescent Nucleic Acid Stain, S11344, life technologies) having binding properties with DNA was mixed so as to have a final concentration of 1 μM. Herein, the DNA structure and the dye were bonded to each other at a concentration ratio of 1:1. The red fluorescent dye used in the present experiment has properties which do not show fluorescence when being present alone, but show fluorescence while being bonded to DNA.

2. Evaluation of In Vivo Distribution (1) Preparation of Animal Tumor Model

A balb/c nude mouse (5 weeks old, male) was used as an experimental animal group, and a tumor was formed by subcutaneously inoculating SCC7 cells ($1.0 \times 10^6$ cells suspended in the culture medium) into the left thigh of the mouse. When the tumor volume became 50 $mm^3$ or more, the tumor was used for the experiment.

(2) In Vivo and Ex Vivo Imaging

A sample of the L-DNA nanostructure (a final concentration of 1 μM, 200 μL) labeled with fluorescence prepared in 1 was injected into the caudal vein of the mouse tumor model (I. V. injection). When compared to the case before the sample was injected, a change in in vivo distribution of the nanostructure was observed by using an IVIS imaging system apparatus at immediately after injection (0 min), 5, 10, 15, 20, 25, and 30 minutes, and 1, 2, 3, 4, 5, 6, 7, 8, 24, and 48 hours (filter set: Ex=640 nm, Em=680 nm), and the results are each shown in FIGS. 7a to 7f (FIG. 7a: Free dye, FIG. 7b: L-Td, FIG. 7c: L-TP, FIG. 7d: L-Cb, FIG. 7e: L-Od, and FIG. 7f: Comparison of in vivo images of four structures on the same scale).

Based on the in vivo imaging results, ex vivo images were observed by sacrificing the mouse at the time when the fluorescent intensity of each structure in the tumor was highest and removing 6 organs of brain, heart, lung, liver, kidney, and spleen and tumor, and are each shown in FIGS. 8a to 8f (FIG. 8a: Free dye, FIG. 8b: L-Td, FIG. 8c: L-TP, FIG. 8d: L-Cb, FIG. 8e: L-Od, and FIG. 8f: Comparison of ex vivo images of four structures on the same scale).

As a result of the experiment, it could be confirmed that all the four L-DNA nanostructures used in the experiment showed cancer tissue selectivity.

Among them, the best cancer tissue selectivity was found in L-Td, and the next best selectivity was found in this order of L-TP, L-Cb, and L-Od. In the tissue other than the cancer tissue, it was found that L-structures were usually found from the kidney.

III. Evaluation of Selective Delivery of Drug to Cancer Tissue In Vivo (1) Optimal Binding Ratio Using Job Plot In order to confirm the optimal binding ratio of Td and doxorubicin (DOX), the Job's plot method was used as in FIG. 9 (see analytical chemistry, 1971, 43, 1265, FIG. 9a: L-Td55 and FIG. 9b: L-Td92). Td and DOX were prepared at a concentration of 1 μM, respectively, in the case of L-Td55 and at a concentration of 1 μM and 3 μM, respectively, in the case of L-Td92, mixed at each volume ratio (see the following Table 6, and the total volume was fixed at 100 μl), and then incubated at normal temperature for 1 hour.

TABLE 6

| Sample | | | | | | | | | | | | |
|---|---|---|---|---|---|---|---|---|---|---|---|---|
| (Td-DOX Complex) | Td | 10 | 9 | 8 | 7 | 6 | 5 | 4 | 3 | 2 | 1 | 0 |
| | DOX | 0 | 1 | 2 | 3 | 4 | 5 | 6 | 7 | 8 | 9 | 10 Total: 100 μl |
| Control | TM buffer | 10 | 9 | 8 | 7 | 6 | 5 | 4 | 3 | 2 | 1 | 0 |
| (free DOX) | DOX | 0 | 1 | 2 | 3 | 4 | 5 | 6 | 7 | 8 | 9 | 10 Total: 100 μl |

And then, the samples were scanned at a wavelength of 200 to 800 nm by using an UV-visible spectrophotometer, and free DOX to which a TM buffer was added instead of the Td sample was used as a control. At 480 nm where the highest absorbance value of DOX was shown, it was judged that the binding ratio used in the sample in which the difference in absorbance values of free DOX and Dox loaded Td was highest formed a composite best, and at a ratio thus determined, DOX was loaded into Td.

(2) Establishment of Xenograft Tumor Model

A balb/c nude mouse (5 weeks old, male) was used as an experimental animal group, and a tumor was formed by subcutaneously inoculating SCC7 cells ($1.0 \times 10^6$ cells suspended in the culture medium) into the left thigh of the mouse. When the tumor volume became approximately 50 mm³, the tumor was used for the experiment.

(3) Cancer Tissue Selective DOX and Therapy

For the selective therapy of cancer tissue, DOX was each loaded into L-Td55 and L-Td92, which are a carrier having cancer tissue selectivity. A sample was prepared by mixing the nanostructure with DOX at the optimal binding ratio obtained through the Job plot method of the slide #1 (L-Td55: DOX=1:24, L-Td92: DOX=1:48).

The therapy experiment was performed by classifying the mice into total six groups (PBS, L-Td55, L-Td92, free DOX, DOX@L-Td55, and DOX@L-Td92), and 7 mice per group were used. Before the therapy was performed each time, the tumor volume and the mouse body weight were measured. In this case, the tumor volume was calculated by a method of (minor axis²*major axis)/2. Each sample was injected into the caudal vein of the mice completely subjected to measurement (see Slide #2 for concentration), the therapy was performed once every three days, and the therapy was performed total 6 times. On day 18 which was 3 days after the last 6th therapy, the final tumor weight was measured by measuring the tumor volume and the mouse body weight, and then measuring the mouse body weight to remove the tumor, and the results are shown in FIGS. 11 and 12 (FIG. 11: Photographs of external parts of mice and a photograph of tumors removed, FIG. 12*a*: Change in volume of tumor, FIG. 12*b*: Change in body weight, FIG. 12*c*: Number of survived m ice, and FIG. 12*d*: Final tumor weight).

(4) Tissue Fragment Experiment (Histological Analysis)

The therapy was finished, and 6 organs of brain, heart, lung, liver, kidney, and spleen and tumor were removed by sacrificing the survived mouse for each group, thereby observing the presence of organ damage and the tumor state. All the organs and tumor were fixed in 4% formaldehyde (4° C., overnight), and then embedded in paraffin after the tissue dehydration process. The paraffin block thus prepared was cut into a thickness of 5 μm, stained with hematoxylin and eosin, and observed through optical microscopy, and the results are shown in FIG. 13.

As a result of the experiment, it was confirmed that tumors were increased 4 to 5 times in the case of DOX@L55 and DOX@L92, while tumor volumes were increased up to about 40 times for the other groups, and thus the growth in tumor was delayed when DOX was loaded into the carrier.

Due to the tumor growth rate of the tumor bearing mice using SCC7 known to be rapidly growing, it was judged that an increase in tumor volume had been observed in all the cases. When a tumor model is established using human-derived cells, a much better therapeutic effect is expected.

For the control which was not subjected to therapy, the L55 treatment group, the L92 treatment group, and the free DOX treatment group showing slight therapeutic effects, the animal groups of individual 1 to 3 mice died during the therapy period.

When the graph of change in body weight is observed, it is judged that the increase in body weight is due to an increase in tumor volume. When the weights of tumors obtained through ex vivo imaging were compared with each other, the tumor weights of the groups other than DOX@L55 or DOX@L92 exhibited values about 5 times higher than the tumor weights of DOX@L55 or DOX@L92.

When the tissue fragments were observed, no part particularly damaged by DOX had been found in the tissues other than cancer tissues.

The invention claimed is:

1. A method of in vivo delivering a pharmaceutically active ingredient to cancer tissue, comprising:
   administering a self-assembled 3-D nucleic acid nanostructure as a pharmaceutically active ingredient carrier to a subject in need thereof,
   wherein the self-assembled 3-D nucleic acid nanostructure comprises:
      double strand nucleic acids; and
      single strands form the sides of the self-assembled 3-D nucleic acid nanostructure,
   wherein the pharmaceutically active ingredient carrier has an L-DNA triangular prism structure composed of 5 strands of L-DNA self-assembled from the combination of:
      i) a single strand of an L-DNA nucleotide sequence of SEQ ID NO:15;
      ii) a single strand of an L-DNA nucleotide sequence of SEQ ID NO:16;
      iii) a single strand of an L-DNA nucleotide sequence of SEQ ID NO:17;
      iv) a single strand of an L-DNA nucleotide sequence of SEQ ID NO:18; and
      v) a single strand of an L-DNA nucleotide sequence of SEQ ID NO:19, and
   wherein the pharmaceutically active ingredient carrier does not comprise a targeting ligand for the tissue.

2. The method of claim 1, wherein the pharmaceutically active ingredient is an anticancer agent.

3. The method of claim 1, wherein the pharmaceutically active ingredient encapsulated is within the nucleic acid nanostructure or bonded to the backbone of the nucleic acid nanostructure, and thereby delivered to the tissue.

4. A method of in vivo delivering an anticancer agent comprising:
   administering a pharmaceutical composition comprising:
      a self-assembled 3-D nucleic acid nanostructure as an anticancer agent carrier to carry the anticancer agent to a subject in need thereof,
   wherein the self-assembled 3-D nucleic acid nanostructure comprises:
      double strand nucleic acids; and
      single strands form the sides of the self-assembled 3-D nucleic acid nanostructure,
   wherein the anticancer agent carrier has an L-DNA triangular prism structure composed of 5 strands of L-DNA self-assembled from the combination of:
      i) a single strand of an L-DNA nucleotide sequence of SEQ ID NO:15;
      ii) a single strand of an L-DNA nucleotide sequence of SEQ ID NO:16;
      iii) a single strand of an L-DNA nucleotide sequence of SEQ ID NO:17;
      iv) a single strand of an L-DNA nucleotide sequence of SEQ ID NO:18; and
      v) a single strand of an L-DNA nucleotide sequence of SEQ ID NO:19, and
   wherein the anticancer agent carrier does not comprise a targeting ligand for the tissue.

5. The method of claim 1, wherein each single strand is connected by linker.

6. The method of claim 2, wherein the anticancer agent is doxorubicin.

7. The method of claim 4, wherein the anticancer agent is doxorubicin.

8. The method of claim 1, the self-assembled 3-D nucleic acid nanostructure is mixed with a pharmaceutical acceptable carrier selected from the group consisting of gum acacia, methyl hydroxybenzoate, and propyl hydroxybenzoate.

9. The method of claim 4, the self-assembled 3-D nucleic acid nanostructure is mixed with a pharmaceutical acceptable carrier selected from the group consisting of gum acacia, methyl hydroxybenzoate, and propyl hydroxybenzoate.

* * * * *